United States Patent

Hashino et al.

[11] Patent Number: 5,824,547
[45] Date of Patent: Oct. 20, 1998

[54] METHOD FOR PRODUCTION OF TRANSFECTED CELLS

[75] Inventors: Kimikazu Hashino, Takatsuki; Hideyuki Matsushita, Kusatsu; Ikunoshin Kato, Uji, all of Japan

[73] Assignee: Takara Shuzo Co., Ltd., Kyoto, Japan

[21] Appl. No.: 836,854

[22] PCT Filed: Nov. 29, 1995

[86] PCT No.: PCT/JP95/02425

§ 371 Date: May 22, 1997

§ 102(e) Date: May 22, 1997

[87] PCT Pub. No.: WO96/17073

PCT Pub. Date: Jun. 6, 1996

[30] Foreign Application Priority Data

Nov. 29, 1994 [JP] Japan .................................. 6-317721

[51] Int. Cl.⁶ .............................. C12N 5/02; C12N 5/10; C12N 5/16; C12N 5/22
[52] U.S. Cl. .................. 435/325; 435/243; 435/374; 435/395; 435/402
[58] Field of Search .................. 435/325, 374, 435/395, 402, 243

[56] References Cited

U.S. PATENT DOCUMENTS

| | | | |
|---|---|---|---|
| 5,045,631 | 9/1991 | Kimizuka et al. | 530/350 |
| 5,049,658 | 9/1991 | Kimizuka et al. | 530/350 |
| 5,102,988 | 4/1992 | Kimizuka et al. | 530/350 |
| 5,136,023 | 8/1992 | Hashino et al. | 530/350 |
| 5,198,423 | 3/1993 | Taguchi et al. | 514/12 |
| 5,302,701 | 4/1994 | Hashi et al. | 530/399 |

FOREIGN PATENT DOCUMENTS

| | | |
|---|---|---|
| 0 463 508 | 1/1992 | European Pat. Off. . |
| 04-063597 | 2/1992 | Japan . |
| 06-090771 | 4/1994 | Japan . |

OTHER PUBLICATIONS

Tur–Kaspa et al, "Use of Electroporation to Introduce Biologically Active Foreign Genes into Primary Rat Hepatocytes", *Molecular and Cellular Biology*, 6:716–718 (1986).

Neumann et al., "Gene Transfer Into Mouse Lyoma Cells by Electroporation in High Electric Fields", The EMBO Journal, vol. 1, No. 7, pp. 841–845, 1982.

Capecchi, "High Efficiency Transformation by Direct Microinjection of DNA into Cultured Mammalian Cells", Cell, vol. 22, part 2, pp. 479–488, 1980.

Sanford et al., "An Improved, Helium–Driven Biolistic Device", Technique–A Journal of Methods in Cell and Molecular Biology, vol. 3, No. 1, pp. 3–16, Feb. 1991.

Williams et al., "Fibronectin and VLA–4 in Haematopoietic Stem Cell–Microenvironment Interactions", Nature, vol. 352, pp. 438–441, Aug. 1, 1991.

*Primary Examiner*—Nancy Degen
*Attorney, Agent, or Firm*—Browdy and Neimark

[57] ABSTRACT

A method is disclosed for the efficient production of a transfected cell which comprises a step of culturing transfected cells in the presence of a cell-adhesive substance, after injection of a foreign gene into target cells, upon production of the transfected cells by transfer of a foreign gene into the target cells through cell perforation. Also provided are transfected cells produced by the method, and a kit for the production of transfected cells that includes a cell-adhesive substance as an essential component, which kit is suitable for use with the method for the efficient production of transfected cells by cell perforation.

12 Claims, 1 Drawing Sheet

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg Gly Asp Ser
1

( 2 ) INFORMATION FOR SEQ ID NO: 2:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Asp Glu Leu Pro Gln Leu Val Thr Leu Pro His Pro Asn Leu His
1                          5                              10                            15

Gly Pro Glu Ile Leu Asp Val Pro Ser Thr
                    20                                25

( 2 ) INFORMATION FOR SEQ ID NO: 3:

(i) SEQUENCE CHARACTERISTICS:
  (A) LENGTH: 274 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:3:

| Pro | Thr | Asp | Leu | Arg | Phe | Thr | Asn | Ile | Gly | Pro | Asp | Thr | Met | Arg |
|---|---|---|---|---|---|---|---|---|---|---|---|---|---|---|
| 1 |  |  |  | 5 |  |  |  |  | 10 |  |  |  |  | 15 |
| Val | Thr | Trp | Ala | Pro | Pro | Pro | Ser | Ile | Asp | Leu | Thr | Asn | Phe | Leu |
|  |  |  |  | 20 |  |  |  |  | 25 |  |  |  |  | 30 |
| Val | Arg | Tyr | Ser | Pro | Val | Lys | Asn | Glu | Glu | Asp | Val | Ala | Glu | Leu |
|  |  |  |  | 35 |  |  |  |  | 40 |  |  |  |  | 45 |
| Ser | Ile | Ser | Pro | Ser | Asp | Asn | Ala | Val | Val | Leu | Thr | Asn | Leu | Leu |
|  |  |  |  | 50 |  |  |  |  | 55 |  |  |  |  | 60 |
| Pro | Gly | Thr | Glu | Tyr | Val | Val | Ser | Val | Ser | Ser | Val | Tyr | Glu | Gln |
|  |  |  |  | 65 |  |  |  |  | 70 |  |  |  |  | 75 |
| His | Glu | Ser | Thr | Pro | Leu | Arg | Gly | Arg | Gln | Lys | Thr | Gly | Leu | Asp |
|  |  |  |  | 80 |  |  |  |  | 85 |  |  |  |  | 90 |
| Ser | Pro | Thr | Gly | Ile | Asp | Phe | Ser | Asp | Ile | Thr | Ala | Asn | Ser | Phe |
|  |  |  |  | 95 |  |  |  |  | 100 |  |  |  |  | 105 |
| Thr | Val | His | Trp | Ile | Ala | Pro | Arg | Ala | Thr | Ile | Thr | Gly | Tyr | Arg |
|  |  |  |  | 110 |  |  |  |  | 115 |  |  |  |  | 120 |
| Ile | Arg | His | His | Pro | Glu | His | Phe | Ser | Gly | Arg | Pro | Arg | Glu | Asp |
|  |  |  |  | 125 |  |  |  |  | 130 |  |  |  |  | 135 |
| Arg | Val | Pro | His | Ser | Arg | Asn | Ser | Ile | Thr | Leu | Thr | Asn | Leu | Thr |
|  |  |  |  | 140 |  |  |  |  | 145 |  |  |  |  | 150 |
| Pro | Gly | Thr | Glu | Tyr | Val | Val | Ser | Ile | Val | Ala | Leu | Asn | Gly | Arg |
|  |  |  |  | 155 |  |  |  |  | 160 |  |  |  |  | 165 |
| Glu | Glu | Ser | Pro | Leu | Leu | Ile | Gly | Gln | Gln | Ser | Thr | Val | Ser | Asp |
|  |  |  |  | 170 |  |  |  |  | 175 |  |  |  |  | 180 |
| Val | Pro | Arg | Asp | Leu | Glu | Val | Val | Ala | Ala | Thr | Pro | Thr | Ser | Leu |
|  |  |  |  | 185 |  |  |  |  | 190 |  |  |  |  | 195 |
| Leu | Ile | Ser | Trp | Asp | Ala | Pro | Ala | Val | Thr | Val | Arg | Tyr | Tyr | Arg |
|  |  |  |  | 200 |  |  |  |  | 205 |  |  |  |  | 210 |
| Ile | Thr | Tyr | Gly | Glu | Thr | Gly | Gly | Asn | Ser | Pro | Val | Gln | Glu | Phe |
|  |  |  |  | 215 |  |  |  |  | 220 |  |  |  |  | 225 |
| Thr | Val | Pro | Gly | Ser | Lys | Ser | Thr | Ala | Thr | Ile | Ser | Gly | Leu | Lys |
|  |  |  |  | 230 |  |  |  |  | 235 |  |  |  |  | 240 |
| Pro | Gly | Val | Asp | Tyr | Thr | Ile | Thr | Val | Tyr | Ala | Val | Thr | Gly | Arg |
|  |  |  |  | 245 |  |  |  |  | 250 |  |  |  |  | 255 |
| Gly | Asp | Ser | Pro | Ala | Ser | Ser | Lys | Pro | Ile | Ser | Ile | Asn | Tyr | Arg |
|  |  |  |  | 260 |  |  |  |  | 265 |  |  |  |  | 270 |
| Thr | Glu | Ile | Asp |  |  |  |  |  |  |  |  |  |  |  |

(2) INFORMATION FOR SEQ ID NO: 4:

(i) SEQUENCE CHARACTERISTICS:
  (A) LENGTH: 296 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:4:

| Ala | Ile | Pro | Ala | Pro 5 | Thr | Asp | Leu | Lys | Phe 10 | Thr | Gln | Val | Thr | Pro 15 |
| Thr | Ser | Leu | Ser | Ala 20 | Gln | Trp | Thr | Pro | Pro 25 | Asn | Val | Gln | Leu | Thr 30 |
| Gly | Tyr | Arg | Val | Arg 35 | Val | Thr | Pro | Lys | Glu 40 | Lys | Thr | Gly | Pro | Met 45 |
| Lys | Glu | Ile | Asn | Leu 50 | Ala | Pro | Asp | Ser | Ser 55 | Ser | Val | Val | Val | Ser 60 |
| Gly | Leu | Met | Val | Ala 65 | Thr | Lys | Tyr | Glu | Val 70 | Ser | Val | Tyr | Ala | Leu 75 |
| Lys | Asp | Thr | Leu | Thr 80 | Ser | Arg | Pro | Ala | Gln 85 | Gly | Val | Val | Thr | Thr 90 |
| Leu | Glu | Asn | Val | Ser 95 | Pro | Pro | Arg | Arg | Ala 100 | Arg | Val | Thr | Asp | Ala 105 |
| Thr | Glu | Thr | Thr | Ile 110 | Thr | Ile | Ser | Trp | Arg 115 | Thr | Lys | Thr | Glu | Thr 120 |
| Ile | Thr | Gly | Phe | Gln 125 | Val | Asp | Ala | Val | Pro 130 | Ala | Asn | Gly | Gln | Thr 135 |
| Pro | Ile | Gln | Arg | Thr 140 | Ile | Lys | Pro | Asp | Val 145 | Arg | Ser | Tyr | Thr | Ile 150 |
| Thr | Gly | Leu | Gln | Pro 155 | Gly | Thr | Asp | Tyr | Lys 160 | Ile | Tyr | Leu | Tyr | Thr 165 |
| Leu | Asn | Asp | Asn | Ala 170 | Arg | Ser | Ser | Pro | Val 175 | Val | Ile | Asp | Ala | Ser 180 |
| Thr | Ala | Ile | Asp | Ala 185 | Pro | Ser | Asn | Leu | Arg 190 | Phe | Leu | Ala | Thr | Thr 195 |
| Pro | Asn | Ser | Leu | Leu 200 | Val | Ser | Trp | Gln | Pro 205 | Pro | Arg | Ala | Arg | Ile 210 |
| Thr | Gly | Tyr | Ile | Ile 215 | Lys | Tyr | Glu | Lys | Pro 220 | Gly | Ser | Pro | Pro | Arg 225 |
| Glu | Val | Val | Pro | Arg 230 | Pro | Arg | Pro | Gly | Val 235 | Thr | Glu | Ala | Thr | Ile 240 |
| Thr | Gly | Leu | Glu | Pro 245 | Gly | Thr | Glu | Tyr | Thr 250 | Ile | Tyr | Val | Ile | Ala 255 |
| Leu | Lys | Asn | Asn | Gln 260 | Lys | Ser | Glu | Pro | Leu 265 | Ile | Gly | Arg | Lys | Lys 270 |
| Thr | Asp | Glu | Leu | Pro 275 | Gln | Leu | Val | Thr | Leu 280 | Pro | His | Pro | Asn | Leu 285 |
| His | Gly | Pro | Glu | Ile 290 | Leu | Asp | Val | Pro | Ser 295 | Thr | | | | |

( 2 ) INFORMATION FOR SEQ ID NO: 5:

( i ) SEQUENCE CHARACTERISTICS:
        ( A ) LENGTH: 302 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

| Pro 1 | Thr | Asp | Leu | Arg 5 | Phe | Thr | Asn | Ile | Gly 10 | Pro | Asp | Thr | Met | Arg 15 |
| Val | Thr | Trp | Ala | Pro 20 | Pro | Pro | Ser | Ile | Asp 25 | Leu | Thr | Asn | Phe | Leu 30 |
| Val | Arg | Tyr | Ser | Pro | Val | Lys | Asn | Glu | Glu | Asp | Val | Ala | Glu | Leu |

```
                              35                         40                         45
Ser  Ile  Ser  Pro  Ser  Asp  Asn  Ala  Val  Val  Leu  Thr  Asn  Leu  Leu
                    50                        55                             60

Pro  Gly  Thr  Glu  Tyr  Val  Val  Ser  Val  Ser  Ser  Val  Tyr  Glu  Gln
                    65                        70                             75

His  Glu  Ser  Thr  Pro  Leu  Arg  Gly  Arg  Gln  Lys  Thr  Gly  Leu  Asp
                    80                        85                             90

Ser  Pro  Thr  Gly  Ile  Asp  Phe  Ser  Asp  Ile  Thr  Ala  Asn  Ser  Phe
                    95                       100                            105

Thr  Val  His  Trp  Ile  Ala  Pro  Arg  Ala  Thr  Ile  Thr  Gly  Tyr  Arg
                   110                       115                            120

Ile  Arg  His  His  Pro  Glu  His  Phe  Ser  Gly  Arg  Pro  Arg  Glu  Asp
                   125                       130                            135

Arg  Val  Pro  His  Ser  Arg  Asn  Ser  Ile  Thr  Leu  Thr  Asn  Leu  Thr
                   140                       145                            150

Pro  Gly  Thr  Glu  Tyr  Val  Val  Ser  Ile  Val  Ala  Leu  Asn  Gly  Arg
                   155                       160                            165

Glu  Glu  Ser  Pro  Leu  Leu  Ile  Gly  Gln  Gln  Ser  Thr  Val  Ser  Asp
                   170                       175                            180

Val  Pro  Arg  Asp  Leu  Glu  Val  Val  Ala  Ala  Thr  Pro  Thr  Ser  Leu
                   185                       190                            195

Leu  Ile  Ser  Trp  Asp  Ala  Pro  Ala  Val  Thr  Val  Arg  Tyr  Tyr  Arg
                   200                       205                            210

Ile  Thr  Tyr  Gly  Glu  Thr  Gly  Gly  Asn  Ser  Pro  Val  Gln  Glu  Phe
                   215                       220                            225

Thr  Val  Pro  Gly  Ser  Lys  Ser  Thr  Ala  Thr  Ile  Ser  Gly  Leu  Lys
                   230                       235                            240

Pro  Gly  Val  Asp  Tyr  Thr  Ile  Thr  Val  Tyr  Ala  Val  Thr  Gly  Arg
                   245                       250                            255

Gly  Asp  Ser  Pro  Ala  Ser  Ser  Lys  Pro  Ile  Ser  Ile  Asn  Tyr  Arg
                   260                       265                            270

Thr  Glu  Ile  Asp  Lys  Pro  Ser  Asp  Glu  Leu  Pro  Gln  Leu  Val  Thr
                   275                       280                            285

Leu  Pro  His  Pro  Asn  Leu  His  Gly  Pro  Glu  Ile  Leu  Asp  Val  Pro
                   290                       295                            300

Ser  Thr
```

( 2 ) INFORMATION FOR SEQ ID NO: 6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Tyr  Ile  Gly  Ser  Arg
 1                    5
```

( 2 ) INFORMATION FOR SEQ ID NO: 7:

( i ) SEQUENCE CHARACTERISTICS:
        ( A ) LENGTH: 283 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ala Val Pro Pro Pro Thr Asp Leu Arg Phe Thr Asn Ile Gly Pro
 1               5                  10                  15

Asp Thr Met Arg Val Thr Trp Ala Pro Pro Ser Ile Asp Leu
                 20              25                  30

Thr Asn Phe Leu Val Arg Tyr Ser Pro Val Lys Asn Glu Glu Asp
                 35              40                  45

Val Ala Glu Leu Ser Ile Ser Pro Ser Asp Asn Ala Val Val Leu
                 50              55                  60

Thr Asn Leu Leu Pro Gly Thr Glu Tyr Val Val Ser Val Ser Ser
                 65              70                  75

Val Tyr Glu Gln His Glu Ser Thr Pro Leu Arg Gly Arg Gln Lys
                 80              85                  90

Thr Gly Leu Asp Ser Pro Thr Gly Ile Asp Phe Ser Asp Ile Thr
                 95              100                 105

Ala Asn Ser Phe Thr Val His Trp Ile Ala Pro Arg Ala Thr Ile
                 110             115                 120

Thr Gly Tyr Arg Ile Arg His His Pro Glu His Phe Ser Gly Arg
                 125             130                 135

Pro Arg Glu Asp Arg Val Pro His Ser Arg Asn Ser Ile Thr Leu
                 140             145                 150

Thr Asn Leu Thr Pro Gly Thr Glu Tyr Val Val Ser Ile Val Ala
                 155             160                 165

Leu Asn Gly Arg Glu Glu Ser Pro Leu Leu Ile Gly Gln Gln Ser
                 170             175                 180

Thr Val Ser Asp Val Pro Arg Asp Leu Glu Val Val Ala Ala Thr
                 185             190                 195

Pro Thr Ser Leu Leu Ile Ser Trp Asp Ala Pro Ala Val Thr Val
                 200             205                 210

Arg Tyr Tyr Arg Ile Thr Tyr Gly Glu Thr Gly Gly Asn Ser Pro
                 215             220                 225

Val Gln Glu Phe Thr Val Pro Gly Ser Lys Ser Thr Ala Thr Ile
                 230             235                 240

Ser Gly Leu Lys Pro Gly Val Asp Tyr Thr Ile Thr Val Tyr Ala
                 245             250                 255

Val Thr Gly Arg Gly Asp Ser Pro Ala Ser Ser Lys Pro Ile Ser
                 260             265                 270

Ile Asn Tyr Arg Thr Glu Ile Asp Lys Pro Ser Gln Met
                 275             280
```

( 2 ) INFORMATION FOR SEQ ID NO: 8:

( i ) SEQUENCE CHARACTERISTICS:
( A ) LENGTH: 279 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

```
Pro Thr Asp Leu Arg Phe Thr Asn Ile Gly Pro Asp Thr Met Arg
 1               5                  10                  15

Val Thr Trp Ala Pro Pro Ser Ile Asp Leu Thr Asn Phe Leu
                 20              25                  30
```

| | | | | | | | | | | | | | | |
|---|---|---|---|---|---|---|---|---|---|---|---|---|---|---|
| Val | Arg | Tyr | Ser | Pro 35 | Val | Lys | Asn | Glu 40 | Glu | Asp | Val | Ala | Glu | Leu 45 |
| Ser | Ile | Ser | Pro | Ser 50 | Asp | Asn | Ala | Val 55 | Leu | Thr | Asn | Leu | Leu 60 | |
| Pro | Gly | Thr | Glu | Tyr 65 | Val | Val | Ser | Val | Ser 70 | Val | Tyr | Glu | Gln 75 | |
| His | Glu | Ser | Thr | Pro 80 | Leu | Arg | Gly | Arg 85 | Gln | Lys | Thr | Gly | Leu | Asp 90 |
| Ser | Pro | Thr | Gly | Ile 95 | Asp | Phe | Ser | Asp 100 | Ile | Thr | Ala | Asn | Ser | Phe 105 |
| Thr | Val | His | Trp | Ile 110 | Ala | Pro | Arg | Ala 115 | Thr | Ile | Thr | Gly | Tyr | Arg 120 |
| Ile | Arg | His | His | Pro 125 | Glu | His | Phe | Ser 130 | Gly | Arg | Pro | Arg | Glu | Asp 135 |
| Arg | Val | Pro | His | Ser 140 | Arg | Asn | Ser | Ile 145 | Thr | Leu | Thr | Asn | Leu | Thr 150 |
| Pro | Gly | Thr | Glu | Tyr 155 | Val | Val | Ser | Ile 160 | Val | Ala | Leu | Asn | Gly | Arg 165 |
| Glu | Glu | Ser | Pro | Leu 170 | Leu | Ile | Gly | Gln 175 | Gln | Ser | Thr | Val | Ser | Asp 180 |
| Val | Pro | Arg | Asp | Leu 185 | Glu | Val | Val | Ala 190 | Ala | Thr | Pro | Thr | Ser | Leu 195 |
| Leu | Ile | Ser | Trp | Asp 200 | Ala | Pro | Ala | Val 205 | Thr | Val | Arg | Tyr | Tyr | Arg 210 |
| Ile | Thr | Tyr | Gly | Glu 215 | Thr | Gly | Gly | Asn 220 | Ser | Pro | Val | Gln | Glu | Phe 225 |
| Thr | Val | Pro | Gly | Ser 230 | Lys | Ser | Thr | Ala 235 | Thr | Ile | Ser | Gly | Leu | Lys 240 |
| Pro | Gly | Val | Asp | Tyr 245 | Thr | Ile | Thr | Val 250 | Tyr | Ala | Val | Thr | Gly | Arg 255 |
| Gly | Asp | Ser | Pro | Ala 260 | Ser | Ser | Lys | Pro 265 | Ile | Ser | Ile | Asn | Tyr | Arg 270 |
| Thr | Glu | Ile | Asp | Lys 275 | Pro | Ser | Gln | Met | | | | | | |

( 2 ) INFORMATION FOR SEQ ID NO: 9:

( i ) SEQUENCE CHARACTERISTICS:
        ( A ) LENGTH: 474 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

| | | | | | | | | | | | | | | |
|---|---|---|---|---|---|---|---|---|---|---|---|---|---|---|
| Ala 1 | Val | Pro | Pro | Pro 5 | Thr | Asp | Leu | Arg | Phe 10 | Thr | Asn | Ile | Gly | Pro 15 |
| Asp | Thr | Met | Arg | Val 20 | Thr | Trp | Ala | Pro | Pro 25 | Ser | Ile | Asp | Leu 30 | |
| Thr | Asn | Phe | Leu | Val 35 | Arg | Tyr | Ser | Pro | Val 40 | Lys | Asn | Glu | Glu | Asp 45 |
| Val | Ala | Glu | Leu | Ser 50 | Ile | Ser | Pro | Ser 55 | Asp | Asn | Ala | Val | Val | Leu 60 |
| Thr | Asn | Leu | Leu | Pro 65 | Gly | Thr | Glu | Tyr 70 | Val | Val | Ser | Val | Ser 75 | |
| Val | Tyr | Glu | Gln | His | Glu | Ser | Thr | Pro | Leu | Arg | Gly | Arg | Gln | Lys |

|  |  |  |  | 80 |  |  |  | 85 |  |  |  | 90 |
|---|---|---|---|---|---|---|---|---|---|---|---|---|
| Thr | Gly | Leu | Asp | Ser | Pro | Thr | Gly | Ile | Asp | Phe | Ser | Asp | Ile | Thr |
|  |  |  |  | 95 |  |  |  | 100 |  |  |  | 105 |
| Ala | Asn | Ser | Phe | Thr | Val | His | Trp | Ile | Ala | Pro | Arg | Ala | Thr | Ile |
|  |  |  |  | 110 |  |  |  | 115 |  |  |  | 120 |
| Thr | Gly | Tyr | Arg | Ile | Arg | His | His | Pro | Glu | His | Phe | Ser | Gly | Arg |
|  |  |  |  | 125 |  |  |  | 130 |  |  |  | 135 |
| Pro | Arg | Glu | Asp | Arg | Val | Pro | His | Ser | Arg | Asn | Ser | Ile | Thr | Leu |
|  |  |  |  | 140 |  |  |  | 145 |  |  |  | 150 |
| Thr | Asn | Leu | Thr | Pro | Gly | Thr | Glu | Tyr | Val | Val | Ser | Ile | Val | Ala |
|  |  |  |  | 155 |  |  |  | 160 |  |  |  | 165 |
| Leu | Asn | Gly | Arg | Glu | Glu | Ser | Pro | Leu | Leu | Ile | Gly | Gln | Gln | Ser |
|  |  |  |  | 170 |  |  |  | 175 |  |  |  | 180 |
| Thr | Val | Ser | Asp | Val | Pro | Arg | Asp | Leu | Glu | Val | Val | Ala | Ala | Thr |
|  |  |  |  | 185 |  |  |  | 190 |  |  |  | 195 |
| Pro | Thr | Ser | Leu | Leu | Ile | Ser | Trp | Asp | Ala | Pro | Ala | Val | Thr | Val |
|  |  |  |  | 200 |  |  |  | 205 |  |  |  | 210 |
| Arg | Tyr | Tyr | Arg | Ile | Thr | Tyr | Gly | Glu | Thr | Gly | Gly | Asn | Ser | Pro |
|  |  |  |  | 215 |  |  |  | 220 |  |  |  | 225 |
| Val | Gln | Glu | Phe | Thr | Val | Pro | Gly | Ser | Lys | Ser | Thr | Ala | Thr | Ile |
|  |  |  |  | 230 |  |  |  | 235 |  |  |  | 240 |
| Ser | Gly | Leu | Lys | Pro | Gly | Val | Asp | Tyr | Thr | Ile | Thr | Val | Tyr | Ala |
|  |  |  |  | 245 |  |  |  | 250 |  |  |  | 255 |
| Val | Thr | Gly | Arg | Gly | Asp | Ser | Pro | Ala | Ser | Ser | Lys | Pro | Ile | Ser |
|  |  |  |  | 260 |  |  |  | 265 |  |  |  | 270 |
| Ile | Asn | Tyr | Arg | Thr | Glu | Ile | Asp | Lys | Pro | Ser | Gln | Asn | Glu | Gly |
|  |  |  |  | 275 |  |  |  | 280 |  |  |  | 285 |
| Leu | Asn | Gln | Pro | Thr | Asp | Asp | Ser | Cys | Phe | Asp | Pro | Tyr | Thr | Val |
|  |  |  |  | 290 |  |  |  | 295 |  |  |  | 300 |
| Ser | His | Tyr | Ala | Val | Gly | Asp | Glu | Trp | Glu | Arg | Met | Ser | Glu | Ser |
|  |  |  |  | 305 |  |  |  | 310 |  |  |  | 315 |
| Gly | Phe | Lys | Leu | Leu | Cys | Gln | Cys | Leu | Gly | Phe | Gly | Ser | Gly | His |
|  |  |  |  | 320 |  |  |  | 325 |  |  |  | 330 |
| Phe | Arg | Cys | Asp | Ser | Ser | Arg | Trp | Cys | His | Asp | Asn | Gly | Val | Asn |
|  |  |  |  | 335 |  |  |  | 340 |  |  |  | 345 |
| Tyr | Lys | Ile | Gly | Glu | Lys | Trp | Asp | Arg | Gln | Gly | Glu | Asn | Gly | Gln |
|  |  |  |  | 350 |  |  |  | 355 |  |  |  | 360 |
| Met | Met | Ser | Cys | Thr | Cys | Leu | Gly | Asn | Gly | Lys | Gly | Glu | Phe | Lys |
|  |  |  |  | 365 |  |  |  | 370 |  |  |  | 375 |
| Cys | Asp | Pro | His | Glu | Ala | Thr | Cys | Tyr | Asp | Asp | Gly | Lys | Thr | Tyr |
|  |  |  |  | 380 |  |  |  | 385 |  |  |  | 390 |
| His | Val | Gly | Glu | Gln | Trp | Gln | Lys | Glu | Tyr | Leu | Gly | Ala | Ile | Cys |
|  |  |  |  | 395 |  |  |  | 400 |  |  |  | 405 |
| Ser | Cys | Thr | Cys | Phe | Gly | Gly | Gln | Arg | Gly | Trp | Arg | Cys | Asp | Asn |
|  |  |  |  | 410 |  |  |  | 415 |  |  |  | 420 |
| Cys | Arg | Arg | Pro | Gly | Gly | Glu | Pro | Ser | Pro | Glu | Gly | Thr | Thr | Gly |
|  |  |  |  | 425 |  |  |  | 430 |  |  |  | 435 |
| Gln | Ser | Tyr | Asn | Gln | Tyr | Ser | Gln | Arg | Tyr | His | Gln | Arg | Thr | Asn |
|  |  |  |  | 440 |  |  |  | 445 |  |  |  | 450 |
| Thr | Asn | Val | Asn | Cys | Pro | Ile | Glu | Cys | Phe | Met | Pro | Leu | Asp | Val |
|  |  |  |  | 455 |  |  |  | 460 |  |  |  | 465 |
| Gln | Ala | Asp | Arg | Glu | Asp | Ser | Arg | Glu |  |  |  |  |  |  |
|  |  |  |  | 470 |  |  |  |  |  |  |  |  |  |  |

( 2 ) INFORMATION FOR SEQ ID NO:10:

( i ) SEQUENCE CHARACTERISTICS:
        ( A ) LENGTH: 385 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Ala Pro Ile Val Asn Lys Val Val Thr Pro Leu Ser Pro Pro Thr
 1               5                  10                  15

Asn Leu His Leu Glu Ala Asn Pro Asp Thr Gly Val Leu Thr Val
                 20                  25                  30

Ser Trp Glu Arg Ser Thr Thr Pro Asp Ile Thr Gly Tyr Arg Ile
                 35                  40                  45

Thr Thr Thr Pro Thr Asn Gly Gln Gln Gly Asn Ser Leu Glu Glu
                 50                  55                  60

Val Val His Ala Asp Gln Ser Ser Cys Thr Phe Asp Asn Leu Ser
                 65                  70                  75

Pro Gly Leu Glu Tyr Asn Val Ser Val Tyr Thr Val Lys Asp Asp
                 80                  85                  90

Lys Glu Ser Val Pro Ile Ser Asp Thr Ile Ile Pro Ala Val Pro
                 95                 100                 105

Pro Pro Thr Asp Leu Arg Phe Thr Asn Ile Gly Pro Asp Thr Met
                110                 115                 120

Arg Val Thr Trp Ala Pro Pro Pro Ser Ile Asp Leu Thr Asn Phe
                125                 130                 135

Leu Val Arg Tyr Ser Pro Val Lys Asn Glu Glu Asp Val Ala Glu
                140                 145                 150

Leu Ser Ile Ser Pro Ser Asp Asn Ala Val Val Leu Thr Asn Leu
                155                 160                 165

Leu Pro Gly Thr Glu Tyr Val Val Ser Val Ser Ser Val Tyr Glu
                170                 175                 180

Gln His Glu Ser Thr Pro Leu Arg Gly Arg Gln Lys Thr Gly Leu
                185                 190                 195

Asp Ser Pro Thr Gly Ile Asp Phe Ser Asp Ile Thr Ala Asn Ser
                200                 205                 210

Phe Thr Val His Trp Ile Ala Pro Arg Ala Thr Ile Thr Gly Tyr
                215                 220                 225

Arg Ile Arg His His Pro Glu His Phe Ser Gly Arg Pro Arg Glu
                230                 235                 240

Asp Arg Val Pro His Ser Arg Asn Ser Ile Thr Leu Thr Asn Leu
                245                 250                 255

Thr Pro Gly Thr Glu Tyr Val Val Ser Ile Val Ala Leu Asn Gly
                260                 265                 270

Arg Glu Glu Ser Pro Leu Leu Ile Gly Gln Gln Ser Thr Val Ser
                275                 280                 285

Asp Val Pro Arg Asp Leu Glu Val Val Ala Ala Thr Pro Thr Ser
                290                 295                 300

Leu Leu Ile Ser Trp Asp Ala Pro Ala Val Thr Val Arg Tyr Tyr
                305                 310                 315

Arg Ile Thr Tyr Gly Glu Thr Gly Gly Asn Ser Pro Val Gln Glu
                320                 325                 330

Phe Thr Val Pro Gly Ser Lys Ser Thr Ala Thr Ile Ser Gly Leu
```

|     |     |     |     | 335 |     |     |     |     | 340 |     |     |     |     | 345 |
| --- | --- | --- | --- | --- | --- | --- | --- | --- | --- | --- | --- | --- | --- | --- |
| Lys | Pro | Gly | Val | Asp | Tyr | Thr | Ile | Thr | Val | Tyr | Ala | Val | Thr | Gly |
|     |     |     |     | 350 |     |     |     |     | 355 |     |     |     |     | 360 |
| Arg | Gly | Asp | Ser | Pro | Ala | Ser | Ser | Lys | Pro | Ile | Ser | Ile | Asn | Tyr |
|     |     |     |     | 365 |     |     |     |     | 370 |     |     |     |     | 375 |
| Arg | Thr | Glu | Ile | Asp | Lys | Pro | Ser | Gln | Met |     |     |     |     |     |
|     |     |     |     | 380 |     |     |     |     | 385 |     |     |     |     |     |

( 2 ) INFORMATION FOR SEQ ID NO:11:

( i ) SEQUENCE CHARACTERISTICS:
        ( A ) LENGTH: 549 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

|     |     |     |     |     |     |     |     |     |     |     |     |     |     |     |
| --- | --- | --- | --- | --- | --- | --- | --- | --- | --- | --- | --- | --- | --- | --- |
| Pro | Thr | Asp | Leu | Arg | Phe | Thr | Asn | Ile | Gly | Pro | Asp | Thr | Met | Arg |
| 1   |     |     |     | 5   |     |     |     |     | 10  |     |     |     |     | 15  |
| Val | Thr | Trp | Ala | Pro | Pro | Pro | Ser | Ile | Asp | Leu | Thr | Asn | Phe | Leu |
|     |     |     |     | 20  |     |     |     |     | 25  |     |     |     |     | 30  |
| Val | Arg | Tyr | Ser | Pro | Val | Lys | Asn | Glu | Glu | Asp | Val | Ala | Glu | Leu |
|     |     |     |     | 35  |     |     |     |     | 40  |     |     |     |     | 45  |
| Ser | Ile | Ser | Pro | Ser | Asp | Asn | Ala | Val | Val | Leu | Thr | Asn | Leu | Leu |
|     |     |     |     | 50  |     |     |     |     | 55  |     |     |     |     | 60  |
| Pro | Gly | Thr | Glu | Tyr | Val | Val | Ser | Val | Ser | Ser | Val | Tyr | Glu | Gln |
|     |     |     |     | 65  |     |     |     |     | 70  |     |     |     |     | 75  |
| His | Glu | Ser | Thr | Pro | Leu | Arg | Gly | Arg | Gln | Lys | Thr | Gly | Leu | Asp |
|     |     |     |     | 80  |     |     |     |     | 85  |     |     |     |     | 90  |
| Ser | Pro | Thr | Gly | Ile | Asp | Phe | Ser | Asp | Ile | Thr | Ala | Asn | Ser | Phe |
|     |     |     |     | 95  |     |     |     |     | 100 |     |     |     |     | 105 |
| Thr | Val | His | Trp | Ile | Ala | Pro | Arg | Ala | Thr | Ile | Thr | Gly | Tyr | Arg |
|     |     |     |     | 110 |     |     |     |     | 115 |     |     |     |     | 120 |
| Ile | Arg | His | His | Pro | Glu | His | Phe | Ser | Gly | Arg | Pro | Arg | Glu | Asp |
|     |     |     |     | 125 |     |     |     |     | 130 |     |     |     |     | 135 |
| Arg | Val | Pro | His | Ser | Arg | Asn | Ser | Ile | Thr | Leu | Thr | Asn | Leu | Thr |
|     |     |     |     | 140 |     |     |     |     | 145 |     |     |     |     | 150 |
| Pro | Gly | Thr | Glu | Tyr | Val | Val | Ser | Ile | Val | Ala | Leu | Asn | Gly | Arg |
|     |     |     |     | 155 |     |     |     |     | 160 |     |     |     |     | 165 |
| Glu | Glu | Ser | Pro | Leu | Leu | Ile | Gly | Gln | Ser | Thr | Val | Ser | Asp |     |
|     |     |     |     | 170 |     |     |     |     | 175 |     |     |     |     | 180 |
| Val | Pro | Arg | Asp | Leu | Glu | Val | Val | Ala | Ala | Thr | Pro | Thr | Ser | Leu |
|     |     |     |     | 185 |     |     |     |     | 190 |     |     |     |     | 195 |
| Leu | Ile | Ser | Trp | Asp | Ala | Pro | Ala | Val | Thr | Val | Arg | Tyr | Tyr | Arg |
|     |     |     |     | 200 |     |     |     |     | 205 |     |     |     |     | 210 |
| Ile | Thr | Tyr | Gly | Glu | Thr | Gly | Gly | Asn | Ser | Pro | Val | Gln | Glu | Phe |
|     |     |     |     | 215 |     |     |     |     | 220 |     |     |     |     | 225 |
| Thr | Val | Pro | Gly | Ser | Lys | Ser | Thr | Ala | Thr | Ile | Ser | Gly | Leu | Lys |
|     |     |     |     | 230 |     |     |     |     | 235 |     |     |     |     | 240 |
| Pro | Gly | Val | Asp | Tyr | Thr | Ile | Thr | Val | Tyr | Ala | Val | Thr | Gly | Arg |
|     |     |     |     | 245 |     |     |     |     | 250 |     |     |     |     | 255 |
| Gly | Asp | Ser | Pro | Ala | Ser | Ser | Lys | Pro | Ile | Ser | Ile | Asn | Tyr | Arg |
|     |     |     |     | 260 |     |     |     |     | 265 |     |     |     |     | 270 |
| Thr | Glu | Ile | Asp | Lys | Pro | Ser | Met | Ala | Ile | Pro | Ala | Pro | Thr | Asp |
|     |     |     |     | 275 |     |     |     |     | 280 |     |     |     |     | 285 |

```
Leu  Lys  Phe  Thr  Gln  Val  Thr  Pro  Thr  Ser  Leu  Ser  Ala  Gln  Trp
               290                      295                          300

Thr  Pro  Pro  Asn  Val  Gln  Leu  Thr  Gly  Tyr  Arg  Val  Arg  Val  Thr
               305                      310                          315

Pro  Lys  Glu  Lys  Thr  Gly  Pro  Met  Lys  Glu  Ile  Asn  Leu  Ala  Pro
               320                      325                          330

Asp  Ser  Ser  Ser  Val  Val  Ser  Gly  Leu  Met  Val  Ala  Thr  Lys
               335                      340                          345

Tyr  Glu  Val  Ser  Val  Tyr  Ala  Leu  Lys  Asp  Thr  Leu  Thr  Ser  Arg
               350                      355                          360

Pro  Ala  Gln  Gly  Val  Val  Thr  Thr  Leu  Glu  Asn  Val  Ser  Pro  Pro
               365                      370                          375

Arg  Arg  Ala  Arg  Val  Thr  Asp  Ala  Thr  Glu  Thr  Thr  Ile  Thr  Ile
               380                      385                          390

Ser  Trp  Arg  Thr  Lys  Thr  Glu  Thr  Ile  Thr  Gly  Phe  Gln  Val  Asp
               395                      400                          405

Ala  Val  Pro  Ala  Asn  Gly  Gln  Thr  Pro  Ile  Gln  Arg  Thr  Ile  Lys
               410                      415                          420

Pro  Asp  Val  Arg  Ser  Tyr  Thr  Ile  Thr  Gly  Leu  Gln  Pro  Gly  Thr
               425                      430                          435

Asp  Tyr  Lys  Ile  Tyr  Leu  Tyr  Thr  Leu  Asn  Asp  Asn  Ala  Arg  Ser
               440                      445                          450

Ser  Pro  Val  Val  Ile  Asp  Ala  Ser  Thr  Ala  Ile  Asp  Ala  Pro  Ser
               455                      460                          465

Asn  Leu  Arg  Phe  Leu  Ala  Thr  Thr  Pro  Asn  Ser  Leu  Leu  Val  Ser
               470                      475                          480

Trp  Gln  Pro  Pro  Arg  Ala  Arg  Ile  Thr  Gly  Tyr  Ile  Ile  Lys  Tyr
               485                      490                          495

Glu  Lys  Pro  Gly  Ser  Pro  Pro  Arg  Glu  Val  Val  Pro  Arg  Pro  Arg
               500                      505                          510

Pro  Gly  Val  Thr  Glu  Ala  Thr  Ile  Thr  Gly  Leu  Glu  Pro  Gly  Thr
               515                      520                          525

Glu  Tyr  Thr  Ile  Tyr  Val  Ile  Ala  Leu  Lys  Asn  Asn  Gln  Lys  Ser
               530                      535                          540

Glu  Pro  Leu  Ile  Gly  Arg  Lys  Lys  Thr
               545
```

( 2 ) INFORMATION FOR SEQ ID NO:12:

( i ) SEQUENCE CHARACTERISTICS:
        ( A ) LENGTH: 422 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Pro  Thr  Asp  Leu  Arg  Phe  Thr  Asn  Ile  Gly  Pro  Asp  Thr  Met  Arg
 1                 5                      10                          15

Val  Thr  Trp  Ala  Pro  Pro  Ser  Ile  Asp  Leu  Thr  Asn  Phe  Leu
               20                       25                           30

Val  Arg  Tyr  Ser  Pro  Val  Lys  Asn  Glu  Glu  Asp  Val  Ala  Glu  Leu
               35                       40                           45

Ser  Ile  Ser  Pro  Ser  Asp  Asn  Ala  Val  Val  Leu  Thr  Asn  Leu  Leu
               50                       55                           60
```

| | | | | | | | | | | | | | | |
|---|---|---|---|---|---|---|---|---|---|---|---|---|---|---|
|Pro|Gly|Thr|Glu|Tyr 65|Val|Val|Ser|Val 70|Ser|Ser|Val|Tyr|Glu|Gln 75|
|His|Glu|Ser|Thr|Pro 80|Leu|Arg|Gly|Arg 85|Gln|Lys|Thr|Gly|Leu|Asp 90|
|Ser|Pro|Thr|Gly|Ile 95|Asp|Phe|Ser|Asp 100|Ile|Thr|Ala|Asn|Ser|Phe 105|
|Thr|Val|His|Trp|Ile 110|Ala|Pro|Arg|Ala 115|Thr|Ile|Thr|Gly|Tyr|Arg 120|
|Ile|Arg|His|His|Pro 125|Glu|His|Phe|Ser 130|Gly|Arg|Pro|Arg|Glu|Asp 135|
|Arg|Val|Pro|His|Ser 140|Arg|Asn|Ser|Ile 145|Thr|Leu|Thr|Asn|Leu|Thr 150|
|Pro|Gly|Thr|Glu|Tyr 155|Val|Val|Ser|Ile 160|Val|Ala|Leu|Asn|Gly|Arg 165|
|Glu|Glu|Ser|Pro|Leu 170|Leu|Ile|Gly|Gln 175|Gln|Ser|Thr|Val|Ser|Asp 180|
|Val|Pro|Arg|Asp|Leu 185|Glu|Val|Val|Ala 190|Ala|Thr|Pro|Thr|Ser|Leu 195|
|Leu|Ile|Ser|Trp|Asp 200|Ala|Pro|Ala|Val 205|Thr|Val|Arg|Tyr|Tyr|Arg 210|
|Ile|Thr|Tyr|Gly|Glu 215|Thr|Gly|Gly|Asn 220|Ser|Pro|Val|Gln|Glu|Phe 225|
|Thr|Val|Pro|Gly|Ser 230|Lys|Ser|Thr|Ala 235|Thr|Ile|Ser|Gly|Leu|Lys 240|
|Pro|Gly|Val|Asp|Tyr 245|Thr|Ile|Thr|Val 250|Tyr|Ala|Val|Thr|Gly|Arg 255|
|Gly|Asp|Ser|Pro|Ala 260|Ser|Ser|Lys|Pro 265|Ile|Ser|Ile|Asn|Tyr|Arg 270|
|Thr|Glu|Ile|Asp|Lys 275|Pro|Ser|Met|Ala 280|Asn|Glu|Gly|Leu|Asn|Gln 285|
|Pro|Thr|Asp|Asp|Ser 290|Cys|Phe|Asp|Pro 295|Tyr|Thr|Val|Ser|His|Tyr 300|
|Ala|Val|Gly|Asp|Glu 305|Trp|Glu|Arg|Met 310|Ser|Glu|Ser|Gly|Phe|Lys 315|
|Leu|Leu|Cys|Gln|Cys 320|Leu|Gly|Phe|Gly 325|Ser|Gly|His|Phe|Arg|Cys 330|
|Asp|Ser|Ser|Arg|Trp 335|Cys|His|Asp|Asn 340|Gly|Val|Asn|Tyr|Lys|Ile 345|
|Gly|Glu|Lys|Trp|Asp 350|Arg|Gln|Gly|Glu 355|Asn|Gly|Gln|Met|Met|Ser 360|
|Cys|Thr|Cys|Leu|Gly 365|Asn|Gly|Lys|Gly 370|Glu|Phe|Lys|Cys|Asp|Pro 375|
|His|Glu|Ala|Thr|Cys 380|Tyr|Asp|Asp|Gly 385|Lys|Thr|Tyr|His|Val|Gly 390|
|Glu|Gln|Trp|Gln|Lys 395|Glu|Tyr|Leu|Gly 400|Ala|Ile|Cys|Ser|Cys|Thr 405|
|Cys|Phe|Gly|Gly|Gln 410|Arg|Gly|Trp|Arg 415|Cys|Asp|Asn|Cys|Arg|Arg 420|
|Pro|Gly| | | | | | | | | | | | | |

( 2 ) INFORMATION FOR SEQ ID NO:13:

( i ) SEQUENCE CHARACTERISTICS:
        ( A ) LENGTH: 332 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:13:

| Pro | Thr | Asp | Leu | Arg | Phe | Thr | Asn | Ile | Gly | Pro | Asp | Thr | Met | Arg |
|---|---|---|---|---|---|---|---|---|---|---|---|---|---|---|
| 1 | | | | 5 | | | | | 10 | | | | | 15 |
| Val | Thr | Trp | Ala | Pro | Pro | Pro | Ser | Ile | Asp | Leu | Thr | Asn | Phe | Leu |
| | | | | 20 | | | | | 25 | | | | | 30 |
| Val | Arg | Tyr | Ser | Pro | Val | Lys | Asn | Glu | Glu | Asp | Val | Ala | Glu | Leu |
| | | | | 35 | | | | | 40 | | | | | 45 |
| Ser | Ile | Ser | Pro | Ser | Asp | Asn | Ala | Val | Val | Leu | Thr | Asn | Leu | Leu |
| | | | | 50 | | | | | 55 | | | | | 60 |
| Pro | Gly | Thr | Glu | Tyr | Val | Val | Ser | Val | Ser | Ser | Val | Tyr | Glu | Gln |
| | | | | 65 | | | | | 70 | | | | | 75 |
| His | Glu | Ser | Thr | Pro | Leu | Arg | Gly | Arg | Gln | Lys | Thr | Gly | Leu | Asp |
| | | | | 80 | | | | | 85 | | | | | 90 |
| Ser | Pro | Thr | Gly | Ile | Asp | Phe | Ser | Asp | Ile | Thr | Ala | Asn | Ser | Phe |
| | | | | 95 | | | | | 100 | | | | | 105 |
| Thr | Val | His | Trp | Ile | Ala | Pro | Arg | Ala | Thr | Ile | Thr | Gly | Tyr | Arg |
| | | | | 110 | | | | | 115 | | | | | 120 |
| Ile | Arg | His | His | Pro | Glu | His | Phe | Ser | Gly | Arg | Pro | Arg | Glu | Asp |
| | | | | 125 | | | | | 130 | | | | | 135 |
| Arg | Val | Pro | His | Ser | Arg | Asn | Ser | Ile | Thr | Leu | Thr | Asn | Leu | Thr |
| | | | | 140 | | | | | 145 | | | | | 150 |
| Pro | Gly | Thr | Glu | Tyr | Val | Val | Ser | Ile | Val | Ala | Leu | Asn | Gly | Arg |
| | | | | 155 | | | | | 160 | | | | | 165 |
| Glu | Glu | Ser | Pro | Leu | Leu | Ile | Gly | Gln | Gln | Ser | Thr | Val | Ser | Asp |
| | | | | 170 | | | | | 175 | | | | | 180 |
| Val | Pro | Arg | Asp | Leu | Glu | Val | Val | Ala | Ala | Thr | Pro | Thr | Ser | Leu |
| | | | | 185 | | | | | 190 | | | | | 195 |
| Leu | Ile | Ser | Trp | Asp | Ala | Pro | Ala | Val | Thr | Val | Arg | Tyr | Tyr | Arg |
| | | | | 200 | | | | | 205 | | | | | 210 |
| Ile | Thr | Tyr | Gly | Glu | Thr | Gly | Gly | Asn | Ser | Pro | Val | Gln | Glu | Phe |
| | | | | 215 | | | | | 220 | | | | | 225 |
| Thr | Val | Pro | Gly | Ser | Lys | Ser | Thr | Ala | Thr | Ile | Ser | Gly | Leu | Lys |
| | | | | 230 | | | | | 235 | | | | | 240 |
| Pro | Gly | Val | Asp | Tyr | Thr | Ile | Thr | Val | Tyr | Ala | Val | Thr | Gly | Arg |
| | | | | 245 | | | | | 250 | | | | | 255 |
| Gly | Asp | Ser | Pro | Ala | Ser | Ser | Lys | Pro | Ile | Ser | Ile | Asn | Tyr | Arg |
| | | | | 260 | | | | | 265 | | | | | 270 |
| Thr | Glu | Ile | Asp | Lys | Pro | Ser | Met | Ala | Asn | Ser | Asp | Ser | Glu | Cys |
| | | | | 275 | | | | | 280 | | | | | 285 |
| Pro | Leu | Ser | His | Asp | Gly | Tyr | Cys | Leu | His | Asp | Gly | Val | Cys | Met |
| | | | | 290 | | | | | 295 | | | | | 300 |
| Tyr | Ile | Glu | Ala | Leu | Asp | Lys | Tyr | Ala | Cys | Asn | Cys | Val | Val | Gly |
| | | | | 305 | | | | | 310 | | | | | 315 |
| Tyr | Ile | Gly | Glu | Arg | Cys | Gln | Tyr | Arg | Asp | Leu | Lys | Trp | Trp | Glu |
| | | | | 320 | | | | | 325 | | | | | 330 |
| Leu | Arg | | | | | | | | | | | | | |

(2) INFORMATION FOR SEQ ID NO:14:

(i) SEQUENCE CHARACTERISTICS:
(A) LENGTH: 341 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:14:

```
Pro  Thr  Asp  Leu  Arg  Phe  Thr  Asn  Ile  Gly  Pro  Asp  Thr  Met  Arg
 1              5                        10                           15
Val  Thr  Trp  Ala  Pro  Pro  Ser  Ile  Asp  Leu  Thr  Asn  Phe  Leu
                20                   25                           30
Val  Arg  Tyr  Ser  Pro  Val  Lys  Asn  Glu  Glu  Asp  Val  Ala  Glu  Leu
                35                        40                           45
Ser  Ile  Ser  Pro  Ser  Asp  Asn  Ala  Val  Val  Leu  Thr  Asn  Leu  Leu
                50                        55                           60
Pro  Gly  Thr  Glu  Tyr  Val  Val  Ser  Val  Ser  Ser  Val  Tyr  Glu  Gln
                65                        70                           75
His  Glu  Ser  Thr  Pro  Leu  Arg  Gly  Arg  Gln  Lys  Thr  Gly  Leu  Asp
                80                        85                           90
Ser  Pro  Thr  Gly  Ile  Asp  Phe  Ser  Asp  Ile  Thr  Ala  Asn  Ser  Phe
                95                       100                          105
Thr  Val  His  Trp  Ile  Ala  Pro  Arg  Ala  Thr  Ile  Thr  Gly  Tyr  Arg
               110                       115                          120
Ile  Arg  His  His  Pro  Glu  His  Phe  Ser  Gly  Arg  Pro  Arg  Glu  Asp
               125                       130                          135
Arg  Val  Pro  His  Ser  Arg  Asn  Ser  Ile  Thr  Leu  Thr  Asn  Leu  Thr
               140                       145                          150
Pro  Gly  Thr  Glu  Tyr  Val  Val  Ser  Ile  Val  Ala  Leu  Asn  Gly  Arg
               155                       160                          165
Glu  Glu  Ser  Pro  Leu  Leu  Ile  Gly  Gln  Gln  Ser  Thr  Val  Ser  Asp
               170                       175                          180
Val  Pro  Arg  Asp  Leu  Glu  Val  Val  Ala  Ala  Thr  Pro  Thr  Ser  Leu
               185                       190                          195
Leu  Ile  Ser  Trp  Asp  Ala  Pro  Ala  Val  Thr  Val  Arg  Tyr  Tyr  Arg
               200                       205                          210
Ile  Thr  Tyr  Gly  Glu  Thr  Gly  Gly  Asn  Ser  Pro  Val  Gln  Glu  Phe
               215                       220                          225
Thr  Val  Pro  Gly  Ser  Lys  Ser  Thr  Ala  Thr  Ile  Ser  Gly  Leu  Lys
               230                       235                          240
Pro  Gly  Val  Asp  Tyr  Thr  Ile  Thr  Val  Tyr  Ala  Val  Thr  Gly  Arg
               245                       250                          255
Gly  Asp  Ser  Pro  Ala  Ser  Ser  Lys  Pro  Ile  Ser  Ile  Asn  Tyr  Arg
               260                       265                          270
Thr  Glu  Ile  Asp  Lys  Pro  Ser  Met  Gly  Ile  Tyr  Ile  Ser  Gly  Met
               275                       280                          285
Ala  Pro  Arg  Pro  Ser  Leu  Thr  Lys  Lys  Gln  Arg  Phe  Arg  His  Arg
               290                       295                          300
Asn  Arg  Lys  Gly  Tyr  Arg  Ser  Gln  Arg  Gly  His  Ser  Arg  Gly  Arg
               305                       310                          315
Asn  Gln  Asn  Ser  Arg  Arg  Pro  Ser  Arg  Ala  Met  Trp  Leu  Ser  Leu
               320                       325                          330
Phe  Ser  Ser  Lys  Asn  Ser  Ser  Ser  Val  Pro  Ala
               335                       340
```

(2) INFORMATION FOR SEQ ID NO:15:

( i ) SEQUENCE CHARACTERISTICS:
    ( A ) LENGTH: 446 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:15:

```
Pro Thr Asp Leu Arg Phe Thr Asn Ile Gly Pro Asp Thr Met Arg
 1               5                  10                  15

Val Thr Trp Ala Pro Pro Ser Ile Asp Leu Thr Asn Phe Leu
                20                  25                  30

Val Arg Tyr Ser Pro Val Lys Asn Glu Glu Asp Val Ala Glu Leu
                35                  40                  45

Ser Ile Ser Pro Ser Asp Asn Ala Val Val Leu Thr Asn Leu Leu
                50                  55                  60

Pro Gly Thr Glu Tyr Val Val Ser Val Ser Val Tyr Glu Gln
                65                  70                  75

His Glu Ser Thr Pro Leu Arg Gly Arg Gln Lys Thr Gly Leu Asp
                80                  85                  90

Ser Pro Thr Gly Ile Asp Phe Ser Asp Ile Thr Ala Asn Ser Phe
                95                 100                 105

Thr Val His Trp Ile Ala Pro Arg Ala Thr Ile Thr Gly Tyr Arg
               110                 115                 120

Ile Arg His His Pro Glu His Phe Ser Gly Arg Pro Arg Glu Asp
               125                 130                 135

Arg Val Pro His Ser Arg Asn Ser Ile Thr Leu Thr Asn Leu Thr
               140                 145                 150

Pro Gly Thr Glu Tyr Val Val Ser Ile Val Ala Leu Asn Gly Arg
               155                 160                 165

Glu Glu Ser Pro Leu Leu Ile Gly Gln Gln Ser Thr Val Ser Asp
               170                 175                 180

Val Pro Arg Asp Leu Glu Val Val Ala Ala Thr Pro Thr Ser Leu
               185                 190                 195

Leu Ile Ser Trp Asp Ala Pro Ala Val Thr Val Arg Tyr Tyr Arg
               200                 205                 210

Ile Thr Tyr Gly Glu Thr Gly Gly Asn Ser Pro Val Gln Glu Phe
               215                 220                 225

Thr Val Pro Gly Ser Lys Ser Thr Ala Thr Ile Ser Gly Leu Lys
               230                 235                 240

Pro Gly Val Asp Tyr Thr Ile Thr Val Tyr Ala Val Thr Gly Arg
               245                 250                 255

Gly Asp Ser Pro Ala Ser Ser Lys Pro Ile Ser Ile Asn Tyr Arg
               260                 265                 270

Thr Glu Ile Asp Lys Pro Ser Met Val Pro Gly Phe Lys Gly Asp
               275                 280                 285

Met Gly Leu Lys Gly Asp Arg Gly Glu Val Gly Gln Ile Gly Pro
               290                 295                 300

Arg Gly Xaa Asp Gly Pro Glu Gly Pro Lys Gly Arg Ala Gly Pro
               305                 310                 315

Thr Gly Asp Pro Gly Pro Ser Gly Gln Ala Gly Glu Lys Gly Lys
               320                 325                 330

Leu Gly Val Pro Gly Leu Pro Gly Tyr Pro Gly Arg Gln Gly Pro
               335                 340                 345

Lys Gly Ser Thr Gly Phe Pro Gly Phe Pro Gly Ala Asn Gly Glu
```

|     |     |     |     | 350 |     |     |     |     | 355 |     |     |     |     | 360 |
| --- | --- | --- | --- | --- | --- | --- | --- | --- | --- | --- | --- | --- | --- | --- |
| Lys | Gly | Ala | Arg | Gly | Val | Ala | Gly | Lys | Pro | Gly | Pro | Arg | Gly | Gln |
|     |     |     |     | 365 |     |     |     |     | 370 |     |     |     |     | 375 |
| Arg | Gly | Pro | Thr | Gly | Pro | Arg | Gly | Ser | Arg | Gly | Ala | Arg | Gly | Pro |
|     |     |     |     | 380 |     |     |     |     | 385 |     |     |     |     | 390 |
| Thr | Gly | Lys | Pro | Gly | Pro | Lys | Gly | Thr | Ser | Gly | Gly | Asp | Gly | Pro |
|     |     |     |     | 395 |     |     |     |     | 400 |     |     |     |     | 405 |
| Pro | Gly | Pro | Pro | Gly | Glu | Arg | Gly | Pro | Gln | Gly | Pro | Gln | Gly | Pro |
|     |     |     |     | 410 |     |     |     |     | 415 |     |     |     |     | 420 |
| Val | Gly | Phe | Pro | Gly | Pro | Lys | Gly | Pro | Pro | Gly | Pro | Pro | Gly | Arg |
|     |     |     |     | 425 |     |     |     |     | 430 |     |     |     |     | 435 |
| Met | Gly | Cys | Pro | Gly | His | Pro | Gly | Gln | Arg | Gly |     |     |     |     |
|     |     |     |     | 440 |     |     |     |     | 445 |     |     |     |     |     |

( 2 ) INFORMATION FOR SEQ ID NO:16:

( i ) SEQUENCE CHARACTERISTICS:
        ( A ) LENGTH: 457 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

| Pro | Thr | Asp | Leu | Arg | Phe | Thr | Asn | Ile | Gly | Pro | Asp | Thr | Met | Arg |
| --- | --- | --- | --- | --- | --- | --- | --- | --- | --- | --- | --- | --- | --- | --- |
| 1   |     |     |     | 5   |     |     |     |     | 10  |     |     |     |     | 15  |
| Val | Thr | Trp | Ala | Pro | Pro | Pro | Ser | Ile | Asp | Leu | Thr | Asn | Phe | Leu |
|     |     |     |     | 20  |     |     |     |     | 25  |     |     |     |     | 30  |
| Val | Arg | Tyr | Ser | Pro | Val | Lys | Asn | Glu | Glu | Asp | Val | Ala | Glu | Leu |
|     |     |     |     | 35  |     |     |     |     | 40  |     |     |     |     | 45  |
| Ser | Ile | Ser | Pro | Ser | Asp | Asn | Ala | Val | Val | Leu | Thr | Asn | Leu | Leu |
|     |     |     |     | 50  |     |     |     |     | 55  |     |     |     |     | 60  |
| Pro | Gly | Thr | Glu | Tyr | Val | Val | Ser | Val | Ser | Ser | Val | Tyr | Glu | Gln |
|     |     |     |     | 65  |     |     |     |     | 70  |     |     |     |     | 75  |
| His | Glu | Ser | Thr | Pro | Leu | Arg | Gly | Arg | Gln | Lys | Thr | Gly | Leu | Asp |
|     |     |     |     | 80  |     |     |     |     | 85  |     |     |     |     | 90  |
| Ser | Pro | Thr | Gly | Ile | Asp | Phe | Ser | Asp | Ile | Thr | Ala | Asn | Ser | Phe |
|     |     |     |     | 95  |     |     |     |     | 100 |     |     |     |     | 105 |
| Thr | Val | His | Trp | Ile | Ala | Pro | Arg | Ala | Thr | Ile | Thr | Gly | Tyr | Arg |
|     |     |     |     | 110 |     |     |     |     | 115 |     |     |     |     | 120 |
| Ile | Arg | His | His | Pro | Glu | His | Phe | Ser | Gly | Arg | Pro | Arg | Glu | Asp |
|     |     |     |     | 125 |     |     |     |     | 130 |     |     |     |     | 135 |
| Arg | Val | Pro | His | Ser | Arg | Asn | Ser | Ile | Thr | Leu | Thr | Asn | Leu | Thr |
|     |     |     |     | 140 |     |     |     |     | 145 |     |     |     |     | 150 |
| Pro | Gly | Thr | Glu | Tyr | Val | Val | Ser | Ile | Val | Ala | Leu | Asn | Gly | Arg |
|     |     |     |     | 155 |     |     |     |     | 160 |     |     |     |     | 165 |
| Glu | Glu | Ser | Pro | Leu | Leu | Ile | Gly | Gln | Gln | Ser | Thr | Val | Ser | Asp |
|     |     |     |     | 170 |     |     |     |     | 175 |     |     |     |     | 180 |
| Val | Pro | Arg | Asp | Leu | Glu | Val | Val | Ala | Ala | Thr | Pro | Thr | Ser | Leu |
|     |     |     |     | 185 |     |     |     |     | 190 |     |     |     |     | 195 |
| Leu | Ile | Ser | Trp | Asp | Ala | Pro | Ala | Val | Thr | Val | Arg | Tyr | Tyr | Arg |
|     |     |     |     | 200 |     |     |     |     | 205 |     |     |     |     | 210 |
| Ile | Thr | Tyr | Gly | Glu | Thr | Gly | Gly | Asn | Ser | Pro | Val | Gln | Glu | Phe |
|     |     |     |     | 215 |     |     |     |     | 220 |     |     |     |     | 225 |
| Thr | Val | Pro | Gly | Ser | Lys | Ser | Thr | Ala | Thr | Ile | Ser | Gly | Leu | Lys |
|     |     |     |     | 230 |     |     |     |     | 235 |     |     |     |     | 240 |

```
Pro  Gly  Val  Asp  Tyr  Thr  Ile  Thr  Val  Tyr  Ala  Val  Thr  Gly  Arg
                    245                      250                      255

Gly  Asp  Ser  Pro  Ala  Ser  Ser  Lys  Pro  Ile  Ser  Ile  Asn  Tyr  Arg
                    260                      265                      270

Thr  Glu  Ile  Asp  Lys  Pro  Ser  Met  Asn  Val  Ser  Pro  Pro  Arg  Arg
                    275                      280                      285

Ala  Arg  Val  Thr  Asp  Ala  Thr  Glu  Thr  Thr  Ile  Thr  Ile  Ser  Trp
                    290                      295                      300

Arg  Thr  Lys  Thr  Glu  Thr  Ile  Thr  Gly  Phe  Gln  Val  Asp  Ala  Val
                    305                      310                      315

Pro  Ala  Asn  Gly  Gln  Thr  Pro  Ile  Gln  Arg  Thr  Ile  Lys  Pro  Asp
                    320                      325                      330

Val  Arg  Ser  Tyr  Thr  Ile  Thr  Gly  Leu  Gln  Pro  Gly  Thr  Asp  Tyr
                    335                      340                      345

Lys  Ile  Tyr  Leu  Tyr  Thr  Leu  Asn  Asp  Asn  Ala  Arg  Ser  Ser  Pro
                    350                      355                      360

Val  Val  Ile  Asp  Ala  Ser  Thr  Ala  Ile  Asp  Ala  Pro  Ser  Asn  Leu
                    365                      370                      375

Arg  Phe  Leu  Ala  Thr  Thr  Pro  Asn  Ser  Leu  Leu  Val  Ser  Trp  Gln
                    380                      385                      390

Pro  Pro  Arg  Ala  Arg  Ile  Thr  Gly  Tyr  Ile  Ile  Lys  Tyr  Glu  Lys
                    395                      400                      405

Pro  Gly  Ser  Pro  Pro  Arg  Glu  Val  Val  Pro  Arg  Pro  Arg  Pro  Gly
                    410                      415                      420

Val  Thr  Glu  Ala  Thr  Ile  Thr  Gly  Leu  Glu  Pro  Gly  Thr  Glu  Tyr
                    425                      430                      435

Thr  Ile  Tyr  Val  Ile  Ala  Leu  Lys  Asn  Asn  Gln  Lys  Ser  Glu  Pro
                    440                      445                      450

Leu  Ile  Gly  Arg  Lys  Lys  Thr
                    455
```

( 2 ) INFORMATION FOR SEQ ID NO:17:

( i ) SEQUENCE CHARACTERISTICS:
        ( A ) LENGTH: 368 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Pro  Thr  Asp  Leu  Arg  Phe  Thr  Asn  Ile  Gly  Pro  Asp  Thr  Met  Arg
  1                 5                       10                       15

Val  Thr  Trp  Ala  Pro  Pro  Ser  Ile  Asp  Leu  Thr  Asn  Phe  Leu
                    20                      25                       30

Val  Arg  Tyr  Ser  Pro  Val  Lys  Asn  Glu  Asp  Val  Ala  Glu  Leu
                    35                      40                       45

Ser  Ile  Ser  Pro  Ser  Asp  Asn  Ala  Val  Val  Leu  Thr  Asn  Leu  Leu
                    50                      55                       60

Pro  Gly  Thr  Glu  Tyr  Val  Val  Ser  Val  Ser  Ser  Val  Tyr  Glu  Gln
                    65                      70                       75

His  Glu  Ser  Thr  Pro  Leu  Arg  Gly  Arg  Gln  Lys  Thr  Gly  Leu  Asp
                    80                      85                       90

Ser  Pro  Thr  Gly  Ile  Asp  Phe  Ser  Asp  Ile  Thr  Ala  Asn  Ser  Phe
                    95                      100                      105
```

| | | | | | | | | | | | | | | |
|---|---|---|---|---|---|---|---|---|---|---|---|---|---|---|
| Thr | Val | His | Trp | Ile 110 | Ala | Pro | Arg | Ala | Thr 115 | Ile | Thr | Gly | Tyr | Arg 120 |
| Ile | Arg | His | His | Pro 125 | Glu | His | Phe | Ser | Gly 130 | Arg | Pro | Arg | Glu | Asp 135 |
| Arg | Val | Pro | His | Ser 140 | Arg | Asn | Ser | Ile | Thr 145 | Leu | Thr | Asn | Leu | Thr 150 |
| Pro | Gly | Thr | Glu | Tyr 155 | Val | Val | Ser | Ile | Val 160 | Ala | Leu | Asn | Gly | Arg 165 |
| Glu | Glu | Ser | Pro | Leu 170 | Leu | Ile | Gly | Gln | Gln 175 | Ser | Thr | Val | Ser | Asp 180 |
| Val | Pro | Arg | Asp | Leu 185 | Glu | Val | Val | Ala | Ala 190 | Thr | Pro | Thr | Ser | Leu 195 |
| Leu | Ile | Ser | Trp | Asp 200 | Ala | Pro | Ala | Val | Thr 205 | Val | Arg | Tyr | Tyr | Arg 210 |
| Ile | Thr | Tyr | Gly | Glu 215 | Thr | Gly | Gly | Asn | Ser 220 | Pro | Val | Gln | Glu | Phe 225 |
| Thr | Val | Pro | Gly | Ser 230 | Lys | Ser | Thr | Ala | Thr 235 | Ile | Ser | Gly | Leu | Lys 240 |
| Pro | Gly | Val | Asp | Tyr 245 | Thr | Ile | Thr | Val | Tyr 250 | Ala | Val | Thr | Gly | Arg 255 |
| Gly | Asp | Ser | Pro | Ala 260 | Ser | Ser | Lys | Pro | Ile 265 | Ser | Ile | Asn | Tyr | Arg 270 |
| Thr | Glu | Ile | Asp | Lys 275 | Pro | Ser | Met | Ala | Ile 280 | Asp | Ala | Pro | Ser | Asn 285 |
| Leu | Arg | Phe | Leu | Ala 290 | Thr | Thr | Pro | Asn | Ser 295 | Leu | Leu | Val | Ser | Trp 300 |
| Gln | Pro | Pro | Arg | Ala 305 | Arg | Ile | Thr | Gly | Tyr 310 | Ile | Ile | Lys | Tyr | Glu 315 |
| Lys | Pro | Gly | Ser | Pro 320 | Pro | Arg | Glu | Val | Val 325 | Pro | Arg | Pro | Arg | Pro 330 |
| Gly | Val | Thr | Glu | Ala 335 | Thr | Ile | Thr | Gly | Leu 340 | Glu | Pro | Gly | Thr | Glu 345 |
| Tyr | Thr | Ile | Tyr | Val 350 | Ile | Ala | Leu | Lys | Asn 355 | Asn | Gln | Lys | Ser | Glu 360 |
| Pro | Leu | Ile | Gly | Arg 365 | Lys | Lys | Thr | | | | | | | |

( 2 ) INFORMATION FOR SEQ ID NO:18:

( i ) SEQUENCE CHARACTERISTICS:
        ( A ) LENGTH: 367 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

| | | | | | | | | | | | | | | |
|---|---|---|---|---|---|---|---|---|---|---|---|---|---|---|
| Pro 1 | Thr | Asp | Leu | Arg 5 | Phe | Thr | Asn | Ile | Gly 10 | Pro | Asp | Thr | Met | Arg 15 |
| Val | Thr | Trp | Ala | Pro 20 | Pro | Pro | Ser | Ile | Asp 25 | Leu | Thr | Asn | Phe | Leu 30 |
| Val | Arg | Tyr | Ser | Pro 35 | Val | Lys | Asn | Glu | Glu 40 | Asp | Val | Ala | Glu | Leu 45 |
| Ser | Ile | Ser | Pro | Ser 50 | Asp | Asn | Ala | Val | Val 55 | Leu | Thr | Asn | Leu | Leu 60 |
| Pro | Gly | Thr | Glu | Tyr | Val | Val | Ser | Val | Ser | Ser | Val | Tyr | Glu | Gln |

-continued

|  |  |  |  | 65 |  |  |  |  | 70 |  |  |  |  | 75 |
|---|---|---|---|---|---|---|---|---|---|---|---|---|---|---|
| His | Glu | Ser | Thr | Pro | Leu | Arg | Gly | Arg | Gln | Lys | Thr | Gly | Leu | Asp |
|  |  |  |  | 80 |  |  |  |  | 85 |  |  |  |  | 90 |
| Ser | Pro | Thr | Gly | Ile | Asp | Phe | Ser | Asp | Ile | Thr | Ala | Asn | Ser | Phe |
|  |  |  |  | 95 |  |  |  |  | 100 |  |  |  |  | 105 |
| Thr | Val | His | Trp | Ile | Ala | Pro | Arg | Ala | Thr | Ile | Thr | Gly | Tyr | Arg |
|  |  |  |  | 110 |  |  |  |  | 115 |  |  |  |  | 120 |
| Ile | Arg | His | His | Pro | Glu | His | Phe | Ser | Gly | Arg | Pro | Arg | Glu | Asp |
|  |  |  |  | 125 |  |  |  |  | 130 |  |  |  |  | 135 |
| Arg | Val | Pro | His | Ser | Arg | Asn | Ser | Ile | Thr | Leu | Thr | Asn | Leu | Thr |
|  |  |  |  | 140 |  |  |  |  | 145 |  |  |  |  | 150 |
| Pro | Gly | Thr | Glu | Tyr | Val | Val | Ser | Ile | Val | Ala | Leu | Asn | Gly | Arg |
|  |  |  |  | 155 |  |  |  |  | 160 |  |  |  |  | 165 |
| Glu | Glu | Ser | Pro | Leu | Leu | Ile | Gly | Gln | Gln | Ser | Thr | Val | Ser | Asp |
|  |  |  |  | 170 |  |  |  |  | 175 |  |  |  |  | 180 |
| Val | Pro | Arg | Asp | Leu | Glu | Val | Val | Ala | Ala | Thr | Pro | Thr | Ser | Leu |
|  |  |  |  | 185 |  |  |  |  | 190 |  |  |  |  | 195 |
| Leu | Ile | Ser | Trp | Asp | Ala | Pro | Ala | Val | Thr | Val | Arg | Tyr | Tyr | Arg |
|  |  |  |  | 200 |  |  |  |  | 205 |  |  |  |  | 210 |
| Ile | Thr | Tyr | Gly | Glu | Thr | Gly | Gly | Asn | Ser | Pro | Val | Gln | Glu | Phe |
|  |  |  |  | 215 |  |  |  |  | 220 |  |  |  |  | 225 |
| Thr | Val | Pro | Gly | Ser | Lys | Ser | Thr | Ala | Thr | Ile | Ser | Gly | Leu | Lys |
|  |  |  |  | 230 |  |  |  |  | 235 |  |  |  |  | 240 |
| Pro | Gly | Val | Asp | Tyr | Thr | Ile | Thr | Val | Tyr | Ala | Val | Thr | Gly | Arg |
|  |  |  |  | 245 |  |  |  |  | 250 |  |  |  |  | 255 |
| Gly | Asp | Ser | Pro | Ala | Ser | Ser | Lys | Pro | Ile | Ser | Ile | Asn | Tyr | Arg |
|  |  |  |  | 260 |  |  |  |  | 265 |  |  |  |  | 270 |
| Thr | Glu | Ile | Asp | Lys | Pro | Ser | Met | Asn | Val | Ser | Pro | Pro | Arg | Arg |
|  |  |  |  | 275 |  |  |  |  | 280 |  |  |  |  | 285 |
| Ala | Arg | Val | Thr | Asp | Ala | Thr | Glu | Thr | Thr | Ile | Thr | Ile | Ser | Trp |
|  |  |  |  | 290 |  |  |  |  | 295 |  |  |  |  | 300 |
| Arg | Thr | Lys | Thr | Glu | Thr | Ile | Thr | Gly | Phe | Gln | Val | Asp | Ala | Val |
|  |  |  |  | 305 |  |  |  |  | 310 |  |  |  |  | 315 |
| Pro | Ala | Asn | Gly | Gln | Thr | Pro | Ile | Gln | Arg | Thr | Ile | Lys | Pro | Asp |
|  |  |  |  | 320 |  |  |  |  | 325 |  |  |  |  | 330 |
| Val | Arg | Ser | Tyr | Thr | Ile | Thr | Gly | Leu | Gln | Pro | Gly | Thr | Asp | Tyr |
|  |  |  |  | 335 |  |  |  |  | 340 |  |  |  |  | 345 |
| Lys | Ile | Tyr | Leu | Tyr | Thr | Leu | Asn | Asp | Asn | Ala | Arg | Ser | Ser | Pro |
|  |  |  |  | 350 |  |  |  |  | 355 |  |  |  |  | 360 |
| Val | Val | Ile | Asp | Ala | Ser | Thr |  |  |  |  |  |  |  |  |
|  |  |  |  | 365 |  |  |  |  |  |  |  |  |  |  |

(2) INFORMATION FOR SEQ ID NO:19:

(i) SEQUENCE CHARACTERISTICS:
        (A) LENGTH: 464 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

| Pro | Thr | Asp | Leu | Arg | Phe | Thr | Asn | Ile | Gly | Pro | Asp | Thr | Met | Arg |
|---|---|---|---|---|---|---|---|---|---|---|---|---|---|---|
| 1 |  |  |  | 5 |  |  |  |  | 10 |  |  |  |  | 15 |
| Val | Thr | Trp | Ala | Pro | Pro | Pro | Ser | Ile | Asp | Leu | Thr | Asn | Phe | Leu |
|  |  |  |  | 20 |  |  |  |  | 25 |  |  |  |  | 30 |

```
Val Arg Tyr Ser Pro Val Lys Asn Glu Glu Asp Val Ala Glu Leu
                 35                  40                  45

Ser Ile Ser Pro Ser Asp Asn Ala Val Val Leu Thr Asn Leu Leu
                 50                  55                  60

Pro Gly Thr Glu Tyr Val Val Ser Val Ser Ser Val Tyr Glu Gln
                 65                  70                  75

His Glu Ser Thr Pro Leu Arg Gly Arg Gln Lys Thr Gly Leu Asp
                 80                  85                  90

Ser Pro Thr Gly Ile Asp Phe Ser Asp Ile Thr Ala Asn Ser Phe
                 95                 100                 105

Thr Val His Trp Ile Ala Pro Arg Ala Thr Ile Thr Gly Tyr Arg
                110                 115                 120

Ile Arg His His Pro Glu His Phe Ser Gly Arg Pro Arg Glu Asp
                125                 130                 135

Arg Val Pro His Ser Arg Asn Ser Ile Thr Leu Thr Asn Leu Thr
                140                 145                 150

Pro Gly Thr Glu Tyr Val Val Ser Ile Val Ala Leu Asn Gly Arg
                155                 160                 165

Glu Glu Ser Pro Leu Leu Ile Gly Gln Gln Ser Thr Val Ser Asp
                170                 175                 180

Val Pro Arg Asp Leu Glu Val Val Ala Ala Thr Pro Thr Ser Leu
                185                 190                 195

Leu Ile Ser Trp Asp Ala Pro Ala Val Thr Val Arg Tyr Tyr Arg
                200                 205                 210

Ile Thr Tyr Gly Glu Thr Gly Gly Asn Ser Pro Val Gln Glu Phe
                215                 220                 225

Thr Val Pro Gly Ser Lys Ser Thr Ala Thr Ile Ser Gly Leu Lys
                230                 235                 240

Pro Gly Val Asp Tyr Thr Ile Thr Val Tyr Ala Val Thr Gly Arg
                245                 250                 255

Gly Asp Ser Pro Ala Ser Ser Lys Pro Ile Ser Ile Asn Tyr Arg
                260                 265                 270

Thr Glu Ile Asp Lys Pro Ser Met Gly Ile Arg Gly Leu Lys Gly
                275                 280                 285

Thr Lys Gly Glu Lys Gly Glu Asp Gly Phe Pro Gly Phe Lys Gly
                290                 295                 300

Asp Met Gly Ile Lys Gly Asp Arg Gly Glu Ile Gly Pro Pro Gly
                305                 310                 315

Pro Arg Gly Glu Asp Gly Pro Glu Gly Pro Lys Gly Arg Gly Gly
                320                 325                 330

Pro Asn Gly Asp Pro Gly Pro Leu Gly Pro Pro Gly Glu Lys Gly
                335                 340                 345

Lys Leu Gly Val Pro Gly Leu Pro Gly Tyr Pro Gly Arg Gln Gly
                350                 355                 360

Pro Lys Gly Ser Ile Gly Phe Pro Gly Phe Pro Gly Ala Asn Gly
                365                 370                 375

Glu Lys Gly Gly Arg Gly Thr Pro Gly Lys Pro Gly Pro Arg Gly
                380                 385                 390

Gln Arg Gly Pro Thr Gly Pro Arg Gly Glu Arg Gly Pro Arg Gly
                395                 400                 405

Ile Thr Gly Lys Pro Gly Pro Lys Gly Asn Ser Gly Gly Asp Gly
                410                 415                 420

Pro Ala Gly Pro Pro Gly Glu Arg Gly Pro Asn Gly Pro Gln Gly
```

|     |     |     |     | 425 |     |     |     |     | 430 |     |     |     |     | 435 |
| --- | --- | --- | --- | --- | --- | --- | --- | --- | --- | --- | --- | --- | --- | --- |
| Pro | Thr | Gly | Phe | Pro | Gly | Pro | Lys | Gly | Pro | Pro | Gly | Pro | Pro | Gly |
|     |     |     |     | 440 |     |     |     |     | 445 |     |     |     |     | 450 |
| Lys | Asp | Gly | Leu | Pro | Gly | His | Pro | Gly | Gln | Arg | Gly | Glu | Thr |     |
|     |     |     |     | 455 |     |     |     |     | 460 |     |     |     |     |     |

( 2 ) INFORMATION FOR SEQ ID NO:20:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

| Pro | Thr | Asp | Leu | Arg | Phe | Thr | Asn | Ile | Gly | Pro | Asp | Thr | Met | Arg |
| --- | --- | --- | --- | --- | --- | --- | --- | --- | --- | --- | --- | --- | --- | --- |
| 1   |     |     |     | 5   |     |     |     |     | 10  |     |     |     |     | 15  |
| Val | Thr | Trp | Ala | Pro | Pro | Ser | Ile | Asp | Leu | Thr | Asn | Phe | Leu |     |
|     |     |     |     | 20  |     |     |     |     | 25  |     |     |     |     | 30  |
| Val | Arg | Tyr | Ser | Pro | Val | Lys | Asn | Glu | Glu | Asp | Val | Ala | Glu | Leu |
|     |     |     |     | 35  |     |     |     |     | 40  |     |     |     |     | 45  |
| Ser | Ile | Ser | Pro | Ser | Asp | Asn | Ala | Val | Val | Leu | Thr | Asn | Leu | Leu |
|     |     |     |     | 50  |     |     |     |     | 55  |     |     |     |     | 60  |
| Pro | Gly | Thr | Glu | Tyr | Val | Val | Ser | Val | Ser | Ser | Val | Tyr | Glu | Gln |
|     |     |     |     | 65  |     |     |     |     | 70  |     |     |     |     | 75  |
| His | Glu | Ser | Thr | Pro | Leu | Arg | Gly | Arg | Gln | Lys | Thr | Gly | Leu | Asp |
|     |     |     |     | 80  |     |     |     |     | 85  |     |     |     |     | 90  |
| Ser | Pro | Thr | Gly | Ile | Asp | Phe | Ser | Asp | Ile | Thr | Ala | Asn | Ser | Phe |
|     |     |     |     | 95  |     |     |     |     | 100 |     |     |     |     | 105 |
| Thr | Val | His | Trp | Ile | Ala | Pro | Arg | Ala | Thr | Ile | Thr | Gly | Tyr | Arg |
|     |     |     |     | 110 |     |     |     |     | 115 |     |     |     |     | 120 |
| Ile | Arg | His | His | Pro | Glu | His | Phe | Ser | Gly | Arg | Pro | Arg | Glu | Asp |
|     |     |     |     | 125 |     |     |     |     | 130 |     |     |     |     | 135 |
| Arg | Val | Pro | His | Ser | Arg | Asn | Ser | Ile | Thr | Leu | Thr | Asn | Leu | Thr |
|     |     |     |     | 140 |     |     |     |     | 145 |     |     |     |     | 150 |
| Pro | Gly | Thr | Glu | Tyr | Val | Val | Ser | Ile | Val | Ala | Leu | Asn | Gly | Arg |
|     |     |     |     | 155 |     |     |     |     | 160 |     |     |     |     | 165 |
| Glu | Glu | Ser | Pro | Leu | Leu | Ile | Gly | Gln | Gln | Ser | Thr | Val | Ser | Asp |
|     |     |     |     | 170 |     |     |     |     | 175 |     |     |     |     | 180 |
| Val | Pro | Arg | Asp | Leu | Glu | Val | Val | Ala | Ala | Thr | Pro | Thr | Ser | Leu |
|     |     |     |     | 185 |     |     |     |     | 190 |     |     |     |     | 195 |
| Leu | Ile | Ser | Trp | Asp | Ala | Pro | Ala | Val | Thr | Val | Arg | Tyr | Tyr | Arg |
|     |     |     |     | 200 |     |     |     |     | 205 |     |     |     |     | 210 |
| Ile | Thr | Tyr | Gly | Glu | Thr | Gly | Gly | Asn | Ser | Pro | Val | Gln | Glu | Phe |
|     |     |     |     | 215 |     |     |     |     | 220 |     |     |     |     | 225 |
| Thr | Val | Pro | Gly | Ser | Lys | Ser | Thr | Ala | Thr | Ile | Ser | Gly | Leu | Lys |
|     |     |     |     | 230 |     |     |     |     | 235 |     |     |     |     | 240 |
| Pro | Gly | Val | Asp | Tyr | Thr | Ile | Thr | Val | Tyr | Ala | Val | Thr | Gly | Arg |
|     |     |     |     | 245 |     |     |     |     | 250 |     |     |     |     | 255 |
| Gly | Asp | Ser | Pro | Ala | Ser | Ser | Lys | Pro | Ile | Ser | Ile | Asn | Tyr | Arg |
|     |     |     |     | 260 |     |     |     |     | 265 |     |     |     |     | 270 |
| Thr | Glu | Ile | Asp | Lys | Pro | Ser | Met | Ala | Ala | Gly | Ser | Ile | Thr | Thr |
|     |     |     |     | 275 |     |     |     |     | 280 |     |     |     |     | 285 |
| Leu | Pro | Ala | Leu | Pro | Glu | Asp | Gly | Gly | Ser | Gly | Ala | Phe | Pro | Pro |
|     |     |     |     | 290 |     |     |     |     | 295 |     |     |     |     | 300 |

| | | | | | | | | | | | | | | |
|---|---|---|---|---|---|---|---|---|---|---|---|---|---|---|
|Gly|His|Phe|Lys|Asp<br>305|Pro|Lys|Arg|Leu|Tyr<br>310|Cys|Lys|Asn|Gly|Gly<br>315|
|Phe|Phe|Leu|Arg|Ile<br>320|His|Pro|Asp|Gly|Arg<br>325|Val|Asp|Gly|Val|Arg<br>330|
|Glu|Lys|Ser|Asp|Pro<br>335|His|Ile|Lys|Leu|Gln<br>340|Leu|Gln|Ala|Glu|Glu<br>345|
|Arg|Gly|Val|Val|Ser<br>350|Ile|Lys|Gly|Val|Cys<br>355|Ala|Asn|Arg|Tyr|Leu<br>360|
|Ala|Met|Lys|Glu|Asp<br>365|Gly|Arg|Leu|Leu|Ala<br>370|Ser|Lys|Cys|Val|Thr<br>375|
|Asp|Glu|Cys|Phe|Phe<br>380|Phe|Glu|Arg|Leu|Glu<br>385|Ser|Asn|Asn|Tyr|Asn<br>390|
|Thr|Tyr|Arg|Ser|Arg<br>395|Lys|Tyr|Thr|Ser|Trp<br>400|Tyr|Val|Ala|Leu|Lys<br>405|
|Arg|Thr|Gly|Gln|Tyr<br>410|Lys|Leu|Gly|Ser|Lys<br>415|Thr|Gly|Pro|Gly|Gln<br>420|
|Lys|Ala|Ile|Leu|Phe<br>425|Leu|Pro|Met|Ser|Ala<br>430|Lys|Ser| | | |

( 2 ) INFORMATION FOR SEQ ID NO:21:

( i ) SEQUENCE CHARACTERISTICS:
        ( A ) LENGTH: 574 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

| | | | | | | | | | | | | | | |
|---|---|---|---|---|---|---|---|---|---|---|---|---|---|---|
|Pro<br>1|Thr|Asp|Leu|Arg<br>5|Phe|Thr|Asn|Ile|Gly<br>10|Pro|Asp|Thr|Met|Arg<br>15|
|Val|Thr|Trp|Ala|Pro<br>20|Pro|Pro|Ser|Ile|Asp<br>25|Leu|Thr|Asn|Phe|Leu<br>30|
|Val|Arg|Tyr|Ser|Pro<br>35|Val|Lys|Asn|Glu|Glu<br>40|Asp|Val|Ala|Glu|Leu<br>45|
|Ser|Ile|Ser|Pro|Ser<br>50|Asp|Asn|Ala|Val|Val<br>55|Leu|Thr|Asn|Leu|Leu<br>60|
|Pro|Gly|Thr|Glu|Tyr<br>65|Val|Val|Ser|Val|Ser<br>70|Ser|Val|Tyr|Glu|Gln<br>75|
|His|Glu|Ser|Thr|Pro<br>80|Leu|Arg|Gly|Arg|Gln<br>85|Lys|Thr|Gly|Leu|Asp<br>90|
|Ser|Pro|Thr|Gly|Ile<br>95|Asp|Phe|Ser|Asp|Ile<br>100|Thr|Ala|Asn|Ser|Phe<br>105|
|Thr|Val|His|Trp|Ile<br>110|Ala|Pro|Arg|Ala|Thr<br>115|Ile|Thr|Gly|Tyr|Arg<br>120|
|Ile|Arg|His|His|Pro<br>125|Glu|His|Phe|Ser|Gly<br>130|Arg|Pro|Arg|Glu|Asp<br>135|
|Arg|Val|Pro|His|Ser<br>140|Arg|Asn|Ser|Ile|Thr<br>145|Leu|Thr|Asn|Leu|Thr<br>150|
|Pro|Gly|Thr|Glu|Tyr<br>155|Val|Val|Ser|Ile|Val<br>160|Ala|Leu|Asn|Gly|Arg<br>165|
|Glu|Glu|Ser|Pro|Leu<br>170|Leu|Ile|Gly|Gln|Gln<br>175|Ser|Thr|Val|Ser|Asp<br>180|
|Val|Pro|Arg|Asp|Leu<br>185|Glu|Val|Val|Ala|Ala<br>190|Thr|Pro|Thr|Ser|Leu<br>195|

```
Leu Ile Ser Trp Asp Ala Pro Ala Val Thr Val Arg Tyr Tyr Arg
             200             205                     210

Ile Thr Tyr Gly Glu Thr Gly Gly Asn Ser Pro Val Gln Glu Phe
             215             220                     225

Thr Val Pro Gly Ser Lys Ser Thr Ala Thr Ile Ser Gly Leu Lys
             230             235                     240

Pro Gly Val Asp Tyr Thr Ile Thr Val Tyr Ala Val Thr Gly Arg
             245             250                     255

Gly Asp Ser Pro Ala Ser Ser Lys Pro Ile Ser Ile Asn Tyr Arg
             260             265                     270

Thr Glu Ile Asp Lys Pro Ser Met Ala Ile Pro Ala Pro Thr Asp
             275             280                     285

Leu Lys Phe Thr Gln Val Thr Pro Thr Ser Leu Ser Ala Gln Trp
             290             295                     300

Thr Pro Pro Asn Val Gln Leu Thr Gly Tyr Arg Val Arg Val Thr
             305             310                     315

Pro Lys Glu Lys Thr Gly Pro Met Lys Glu Ile Asn Leu Ala Pro
             320             325                     330

Asp Ser Ser Ser Val Val Ser Gly Leu Met Val Ala Thr Lys
             335             340                     345

Tyr Glu Val Ser Val Tyr Ala Leu Lys Asp Thr Leu Thr Ser Arg
             350             355                     360

Pro Ala Gln Gly Val Val Thr Thr Leu Glu Asn Val Ser Pro Pro
             365             370                     375

Arg Arg Ala Arg Val Thr Asp Ala Thr Glu Thr Thr Ile Thr Ile
             380             385                     390

Ser Trp Arg Thr Lys Thr Glu Thr Ile Thr Gly Phe Gln Val Asp
             395             400                     405

Ala Val Pro Ala Asn Gly Gln Thr Pro Ile Gln Arg Thr Ile Lys
             410             415                     420

Pro Asp Val Arg Ser Tyr Thr Ile Thr Gly Leu Gln Pro Gly Thr
             425             430                     435

Asp Tyr Lys Ile Tyr Leu Tyr Thr Leu Asn Asp Asn Ala Arg Ser
             440             445                     450

Ser Pro Val Val Ile Asp Ala Ser Thr Ala Ile Asp Ala Pro Ser
             455             460                     465

Asn Leu Arg Phe Leu Ala Thr Thr Pro Asn Ser Leu Leu Val Ser
             470             475                     480

Trp Gln Pro Pro Arg Ala Arg Ile Thr Gly Tyr Ile Ile Lys Tyr
             485             490                     495

Glu Lys Pro Gly Ser Pro Pro Arg Glu Val Val Pro Arg Pro Arg
             500             505                     510

Pro Gly Val Thr Glu Ala Thr Ile Thr Gly Leu Glu Pro Gly Thr
             515             520                     525

Glu Tyr Thr Ile Tyr Val Ile Ala Leu Lys Asn Asn Gln Lys Ser
             530             535                     540

Glu Pro Leu Ile Gly Arg Lys Lys Thr Asp Glu Leu Pro Gln Leu
             545             550                     555

Val Thr Leu Pro His Pro Asn Leu His Gly Pro Glu Ile Leu Asp
             560             565                     570

Val Pro Ser Thr
```

METHOD FOR PRODUCTION OF TRANSFECTED CELLS

FIELD OF THE INVENTION

The present invention relates to a method for production of transfected cells, more particularly, a method which makes possible to transfer a foreign gene into target cells with high efficiency in the fields such as cell technology, genetic engineering, developmental engineering and the like.

BACKGROUND OF THE INVENTION

As a method for transferring a foreign gene into target cells, there are known a calcium phosphate method, a DEAE-dextran method, a liposome method, an electroporation method, a microinjection method, a particle gun method and the like. All of these methods have both advantages and disadvantages with respect to manipulation procedures, efficiency, damage on cells and the like. Among these methods, a perforation method such as an electroporation method, a microinjection method, a particle gun method and the like enables easy handling of the cells without using special reagents and provides good transfer efficiency. However, damage to cells by perforation cannot be avoided.

The object of the present invention is to provide a method for improving the transfer efficiency when a foreign gene is transferred into target cells by a perforation method to produce transfected cells.

SUMMARY OF THE INVENTION

The first aspect of the present invention relates to a method for the production of transfected cells, which is characterized by comprising a step of culturing the cells in the presence of a cell-adhesive substance, after injection of a foreign gene into target cells using a perforation method.

The second aspect of the present invention relates to transfected cells containing a foreign gene which are produced by the method of the present invention.

The third aspect of the present invention relates to a kit, which is used for a method for the production of transfected cells according to the first aspect of the present invention and is characterized by containing a cell-adhesive substance.

DETAILED DESCRIPTION OF THE INVENTION

Figure 1:
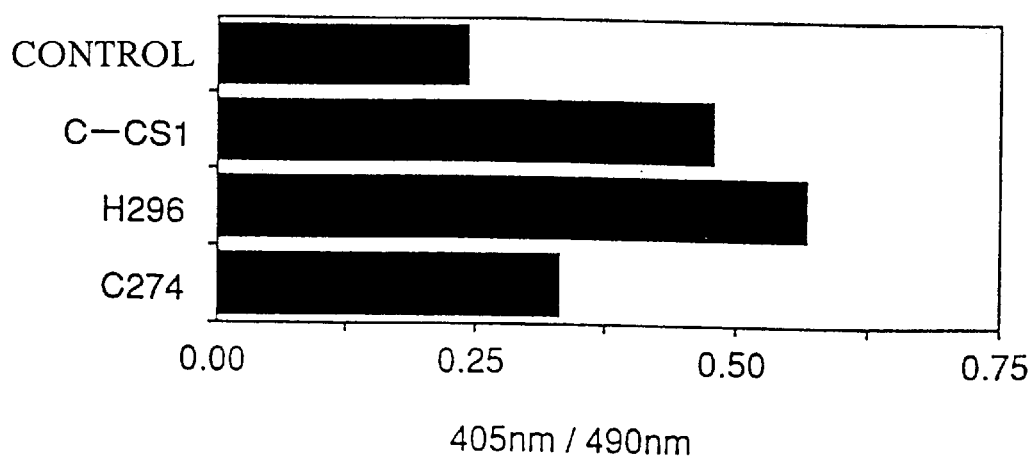
FIG. 1 is a graph showing the effect of cell-adhesive polypeptide treatment on gene transfer efficiency in the transfer of pCAT-control vector into human epidermoid cancer cell A-431.

The method of the present invention is characterized by culturing the cell in the presence of a substance having the cell-adhesive activity after a foreign gene is transferred into target cells using a perforation method.

As used herein, the perforation method means a method for injection of a gene by perforating a cell wall, including an electroporation method, a microinjection method, a particle gun method and the like. The electroporation method is as described in, for example, Tanpakushitsu, Kakusan, Koso, volume 31, pages 1591–1603 (1986). The microinjection method is as described in, for example, *Cell*, volume 22, pages 479–488 (1980). The particle gun method is as described in, for example, *Technique*, volume 3, pages 3–16 (1991). These methods include the known methods used for transferring a gene into cells.

As cells to be used in these perforation methods, for example, there are animal cells which are prepared according to a known method ["Shin-Seikagaku Jikkenkoza 18, Saibobaiyogijyutsu", 1st edition (1990), edited by Nippon Seikagakugakkai, published by Tokyo Kagakudojin] and cultured animal cells may be used.

As used herein, a cell-adhesive substance refers to a substance having the cell-adhesive, that is, the activity to make target cells adhere to a cell, to an extracellular matrix which is a substance filling a space between cells in the tissue, or to a material such as plastic, glass and the like. In the present invention, any substances having the activity can be used as long as they give no adverse effects on transfection of target cells. Such the activity is to fix cells, for example, to culture ware covered with a cell-adhesive substance while maintaining the cell in its form, or in a spreaded form, that is, in the changed form after the cell has been spreaded in one or more directions.

Attachment between the cell-adhesive substance and the target cell can be assayed using a conventional method. The method includes, for example, a method described in *Nature*, 352:438–441 (1991). Briefly, the cell-adhesive substance covers a plastic dish, and a population of cells to be assayed is put into a medium and allowing it to stand for 30 minutes to 2 hours. After this incubation period, non-adhered cells are recovered, counted and assayed for viability. Cells adhered to the cell-adhesive substance are recovered using trypsin or a cell dissociation buffer (for example, Gibco), counted and assayed for viability. Then, a ratio of adhered cells is calculated and compared with a standard control such as a plastic dish covered with bovine serum albumin (BSA). A combination of cell-adhesive substance/cell can be determined by substantial adhesion of the target cell with the cell-adhesive substance assayed. In addition, the cell-spreading activity can be determined by observing a change in the form of the adhered cells under a microscope before dissociating cells using trypsin or a cell dissociation buffer, in the above procedures.

Examples of the cell-adhesive substance include, for example, a cell-adhesive polypeptide or a functional equivalent thereof and a cell-adhesive synthetic polymer.

Examples of the polypeptide to be used in the present invention, having the cell-adhering activity include a cell-adhesive polypeptide such as invasin, polylysine which is not derived from an extracellular matrix, a polypeptide showing the cell-spreading activity described in JP-A 2-311498, components of an extracellular matrix such as fibronectin, laminin, collagen, vitronectin, osteopontin, thrombospondin, tenascin and the like. The extracellular matrix components can be prepared from a natural or cultured source by a known method [*International Journal of Cancer*, volume 20, pages 1–5 (1977); *Journal of Biological Chemistry*, volume 254, pages 9933–9937, (1979); "Zoku-Seikagaku Jikkenkoza", volume 6, Saibokokkaku no Kozo to Kino (Structure and Function of Cell Skeleton) (last volume), (1st edition) (1986) edited by Nippon Seikagakugakkai, published by Tokyo Kagakudojin; *Cell Structure and Function*, volume 13, pages 281–292 (1988); *Journal of Biological Chemistry*, volume 264, pages 18202–18208 (1989); and *Journal of Biological Chemistry*, volume 260, pages 12240–12245 (1985)]. The cell-adhesive polypeptide may be substantially purified extracellular matrices exhibiting the cell-adhering activity, substantially purified extracellular matrix fragments or a mixture thereof. More particularly, proteins and polypeptides having the cell-adhesive or the cell spreading activity, or a functional equivalent thereof, may be used.

As these cell-adhesive polypeptides, substantially purified natural polypeptides, polypeptides from enzymatical or chemical degradation of the natural polypeptides, or the similar polypeptides made by genetic engineering may be used. Further, materials obtained by modifying these polypeptides without impairing the function, that is, the cell-adhering activity or the cell-spreading activity may be used. In the present invention, even if the polypeptide has a deletion, substitution, addition and/or insertion of amino acids in the amino acid sequence of a polypeptide from natural origin, as long as the polypeptide has the desired cell-adhering activity or the cell-spreading activity, it is referred to as a functional equivalent of a polypeptide having the natural amino acid sequence. That is, it is known that naturally occurring proteins include proteins of which amino acid sequences have mutations such as deletions, insertions, additions, substitutions and the like of amino acids, which are due to a modification reaction in the living body after production or during purification, in addition to polymorphism or mutation of genes encoding those naturally occurring proteins. Regardless of these mutations, there are proteins exhibiting the physiological and biological activity substantially equivalent to that of proteins having no mutation. Like this, even when there is a structural difference between polypeptides, as long as they share the common main functions, they are called polypeptides having the functionally equivalent activity.

This is also true where the above mutations are artificially introduced into the amino acid sequence of proteins. In this case, a greater variety of mutants may be made. As long as these mutants exhibit the physiological activity substantially equivalent to that of proteins having no mutations, they are interpreted to be a polypeptide having the functionally equivalent activity.

For example, in many cases, a methionine residue which is present at a N-terminus of a protein expressed in *Escherichia coli* is said to be removed by action of methionine aminopeptidase, thus, generating both proteins having a methionine residue or those having no methionine residue depending upon the kind of proteins. However, whether or not a protein has a methionine residue does not affect the protein activity in many cases. In addition, it is known that a polypeptide, a certain cysteine residue of which is substituted with a serine residue in the amino acid sequence of human interleukin-2 (IL-2), retains the interleukin-2 activity [*Science*, volume 224, page 1431 (1984)].

Further, upon production of proteins by genetic engineering, proteins are frequently expressed as fused proteins. For example, in order to increase an amount of an expressed protein of interest, the protein is expressed by adding a N-terminal peptide chain derived from another protein to the N-terminal of the protein of interest, or adding a suitable peptide chain to the N-terminus or the C-terminus of the protein of interest to facilitate purification of the protein of interest by using a carrier having the affinity to the added peptide chain.

In this respect, the related biotechnological techniques have advanced to a state in which deletion, substitution, addition or other modification of amino acids in a functional region of the polypeptide can be routinely carried out. Then, the resulting amino acid sequence may be routinely screened for the desired cell-adhering activity or the cell-spreading activity according to the above method.

Polypeptides having the cell-adhering activity may be an artificial polypeptide containing, in the molecule, the amino acid sequence necessary for the cell-adhering activity, for example, the amino acid sequence may be selected from the amino acid sequence represented by SEQ ID No:1 (RGDS), the amino acid sequence represented by SEQ ID NO:2 (CS1) and the amino acid sequence represented by SEQ ID NO:6 (central sequence of laminin, YIGSR). These polypeptides can be prepared in a large amount by a genetic engineering method or a chemical synthesis method and may be used as a purified polypeptide.

Examples of the artificial polypeptide having, in the molecule, the amino acid sequence represented by SEQ ID NO:1 include a polypeptide represented by SEQ ID NO:7 described in JP-A 1-180900. The polypeptide can be prepared using *Escherichia coli* HB101/pTF1409 (FERM BP-1939) according to a method described in JP-A 1-180900. In addition polypeptides represented by their respective sequence ID numbers in the sequence list shown in Table 1 below can be prepared according to a genetic engineering method described in each specification.

In addition, a plasmid pCHV90 contained in *Escherichia coli* HB101/pCHV90 in Table 1 can be prepared using *Escherichia coli* HB101/pHD101 (FERM BP-2264) and *Escherichia coli* JM109/pTF7021 (FERM BP-1941) according to a method described in JP-A 5-271291.

TABLE 1

| Laid Open Publication | SEQ ID NO | Living Bacterium (*Escherichia coli*) | Accession No. |
|---|---|---|---|
| JP-A 1-206998 | 8 | JM109/pTF7021 | FERM BP-1941 |
| JP-A 1-261398 | 9 | HB101/pTF1801 | FERM P-9948 |
| JP-A 2-97397 | 3 | JM109/pTF7221 | FERM BP-1915 |
| JP-A 2-152990 | 10 | JM109/pTFB800 | FERM BP-2126 |
| JP-A 2-311498 | 11 | HB101/pCH101 | FERM BP-2799 |
| JP-A 3-59000 | 12 | JM109/pCF406 | FERM P-10837 |
| JP-A 3-232898 | 13 | HB101/pCE102 | FERM P-11226 |
| JP-A 4-54199 | 14 | JM109/pTF7520 + VN-IN.TAA | FERM P-11526 |
|  | 15 | JM109/pTF7520 + Col$^{\times 1}$ | FERM P-11527 |
| JP-A 5-271291 | 16 | HB101/pCHV179 | FERM P-12183 |
|  | 17 | HB101/pCHV90 |  |
|  | 18 | HB101/pCHV89 | FERM P-182 |
| JP-A 5-97698 | 19 | JM109/pTF7520ColV | FERM BP-5277 |
| JP-A 5-178897 | 20 | JM109/pYMH-CF.A | FERM BP-5278 |

Alternatively, artificial polypeptides having, in the molecule, the amino acid sequence represented by SEQ ID NO:1 can be PolyRGDS described, described in JP-A 3-173828, can be synthesized and used.

Examples of artificial polypeptides having, in the molecule, the amino acid sequence represented by SEQ ID NO:2 include a polypeptide represented by SEQ ID NO:4, described in JP-A 2-311498, and the polypeptide can be prepared by genetic engineering using *Escherichia coli* HB101/pHD102 (FERM P-10721) according to a method described in JP-A 2-311498. In addition, a polypeptide represented by SEQ ID NO:2 may be chemically synthesized according to a method described in JP-A 3-284700.

Further, examples of artificial polypeptides having, in the molecule, the amino acid sequence represented by SEQ ID NO:2 and the amino acid sequence represented by SEQ ID NO:3 include a polypeptide represented by SEQ ID NO:21 described in JP-A 2-311498 and the polypeptide can be prepared by genetic engineering using *Escherichia coli* HB101/pCH102 (FERM BP-2800) according to a method described in JP-A 2-311498. In addition, a polypeptide represented by SEQ ID NO:5 described in JP-A 3-284700 is a polypeptide containing, in the molecule, the amino acid sequences of SEQ ID NOs: 1 and 2 and the polypeptide can be prepared by genetic engineering using *Escherichia coli* HB101/pCS25 (FERM P-11339) according to a method described in JP-A 3-284700.

As described above, examples of the polypeptides used in the present invention are cell-adhesive polypeptides containing, in the molecule, the amino acid sequence represented by SEQ ID NO:1 and/or the amino acid sequence represented by SEQ ID NO:2. As the polypeptide, a polypeptide obtained by covalently binding a polypeptide derived from a cell adhesion domain of human fibronectin ["Fibronectin", pages 47–121 (1989), edited by Mosher, D. F., published by Academic Press] with a CS1 polypeptide derived from the same (ibid), a polypeptide derived from a heparin binding domain (ibid) containing a CS1 polypeptide, or a polypeptide derived from a cell adhesion domain can be used, and they can be made by genetic engineering, respectively. For example, respective necessary regions are taken out from a vector containing a DNA encoding a cell adhesion domain-derived polypeptide, a vector containing a DNA encoding a CS1 polypeptide, and a vector containing a DNA encoding a heparin binding domain-derived peptide containing a CS1 polypeptide, respectively, and they can be used alone or in combination thereof to make a vector expressing a polypeptide containing, in the molecule, the amino acid sequence represented by SEQ ID NO:1 and/or the amino acid sequence represented by SEQ ID NO:2.

When a polypeptide, where a polypeptide containing, in the molecule, the amino acid sequence represented by SEQ ID NO:1 and a polypeptide containing, in the molecule, the amino acid sequence represented by SEQ ID NO:2 are covalently bound, is made, a covalent bonding between polypeptides may be a direct bonding or an indirect bonding, for example, an indirect bonding via a spacer. A spacer is an insertion sequence for adjusting an intermolecular distance in each region. As the spacer, an arbitrary peptide chain can be used, for example, a sequence upstream of a CS1 region in the fibronectin molecule. The spacer sequence can be easily introduced therein by genetic engineering.

The cell-adhesive synthetic polymers include the known poly-N-p-vinylbenzyl-D-lactoneamide (PVLA) polymer.

In the present invention, the target cell include, but is not limited to, hematopoietic stem cell, peripheral blood stem cell, umbilical blood cell, ES cell, lymphocyte, cancer cell and the like.

Examples of the foreign gene include, but are not limited to, nucleic acid selected from nucleic acids encoding proteins, nucleic acids encoding polypeptides, antisense DNAs, antisense RNAs, ribozymes, nucleic acids encoding intracellular antibodies and pseudogenes (decoy genes). In the present invention, the foreign gene may be inserted into a vector.

Examples of the vector are retrovirus vector, adenovirus vector, vacciniavirus vector, herpesvirus vector and the like.

According to the present invention a transfected cell with a foreign gene can be obtained with high efficiency by culturing a target cell, into which a foreign gene has been transferred by a perforation method according to a conventional method, in the presence of a cell-adhesive substance. A cell culture method may be selected from the known methods depending upon the cell used. For example, when cell culturing is performed in the presence of a cell-adhesive polypeptide, 250 to 2000 µg/ml of the cell-adhesive polypeptide may be used in a culture medium to culture it according to a conventional method.

Particularly, culturing is preferably carried out using a culture ware covered with a cell-adhesive substance. The culture ware refers to any ware normally used for cell culture, for example, a culture dish, a culture ware using a microcarrier, and a culture ware using fibrous hollow fibers. The culture ware may be covered with the substance by coating or spraying. For example, the culture may be easily covered with the polypeptide by dissolving it in a suitable solution such as a phosphate buffered saline (PBS), adding the solution to the culture ware and allowing it to stand for a suitable period of time. An amount of the polypeptide with which the culture ware is covered may be selected from a range of 50 to 1000 pmol/cm$^2$, suitably 150 to 600 pmol/cm$^2$.

Transfected cells which have been cultured in the presence of the cell-adhesive substance can be obtained from a culture according to a conventional method. Thus, transfected cells can be produced with high efficiency.

The resulting transfected cells are useful for the production of useful substances by cells using recombinant DNA techniques, development of disease models, gene therapy and the like. Thus, transfected cells can be produced with high efficiency according to the present invention.

In addition, the present invention can be simply carried out by using a kit containing a cell-adhesive substance. The cell-adhesive substance to be contained in the kit may be in a form of solutions or lyophilized powders. The kit may contain a buffer for dissolving or diluting the cell-adhesive substance, a cell culture medium, a cell culture ware and the like. For example, a transfected cell can be simply produced by preparing a kit combining polypeptides, PBS for diluting the polypeptide, a cell culture ware and the like which are used for the method of the present invention. A reagent contained in the kit may be in liquid form or in lyophilized form.

A perforation method in the present invention can be used by appropriately selecting from an electroporation method, a microinjection method, a particle gun method and the like depending upon the purpose.

The present invention is illustrated by the non-limiting Examples below.

EXAMPLE 1

1. Coating of culture dish with cell-adhesive polypeptide.

A polypeptide represented by SEQ ID NO:3 (hereinafter referred to as "C274"), a polypeptide represented by SEQ ID NO:4 (hereinafter referred to as H296) and a polypeptide represented by SEQ ID NO:5 (hereinafter referred to as "C·CS1") were each dissolved in a phosphate buffered saline (PBS) to 1 µM, respectively, which were then sterilized using a 0.22 µm filter (Millex-GV, Millipore).

Each 1 ml/well of these solutions was added to a 24-well polystyrene culture dish (manufactured by Corning), respectively, to coat the dish at 4° C. overnight. These dishes were rinsed with a 500μl/well of a Dulbecco's modified minimum basal medium not containing bovine fetal serum prior to the addition of a transformed cell described below.

2. Transfection of cells

Two culture dishes (diameter: 100 mm) of human epidermoid cancer cell A-431 which had been cultured in a Dulbecco's modified minimum basal medium containing 10% bovine fetal serum were rinsed with 10 ml of a Dulbecco's modified minimum basal medium not containing bovine fetal serum, respectively, and 3 ml of PBS containing 0.25% bovine trypsin and 0.02% EDTA was added thereto to detach cells from the culture dish. To these, 7 ml of a Dulbecco's modified minimum basal medium not containing bovine fetal serum was added, followed by centrifugation at 800 rpm for 3 minutes to collect cells. The resulting cells were suspended in 10 ml of a Dulbecco's modified minimum basal medium containing bovine fetal serum, followed by centrifugation at 800 rpm for 3 minutes to collect cells. The resulting cells were combined, suspended in 10 ml of PBS, a 3/10 aliquot of the suspension was taken and divided into two equal aliquots, which were centrifuged at 800 rpm for 3 minutes to collect cells, respectively. The resulting cells were suspended again in 10 ml of PBS, followed by centrifugation at 800 rpm for 3 minutes to collect two batches of cells. One batch of the resulting cells were suspended in 1 ml of PBS containing 15 μg of pCAT-control vector (Promega) which had been aseptically prepared, and placed in an electroporation cuvette for Gene Pulser (BioRad), which was allowed to stand in ice for 10 minutes. The other batch of the resulting cells were suspended in 1 ml of PBS, and placed in an electroporation cuvette for Gene Pulser (BioRad), which was allowed to stand in ice for 10 minutes. Each batch of cells was allowed to stand in ice for 10 minutes, and voltage was applied thereto at 250 V and 960 μF. After application, the cells were allowed to stand in a cuvette in ice for 10 minutes. Thereafter, the cells were recovered into 15 ml 20 of a Dulbecco's modified minimum basal medium containing 10% bovine fetal serum, 1 ml/well of which were added to a 24-well polystyrene culture dish covered with the above polypeptide. These cells were cultured at 37° C. in the presence of 5% $CO_2$ gas overnight, the medium was removed by aspiration, and 1 ml/well of a fresh Dulbecco's modified minimum basal medium containing 10% bovine fetal serum was added thereto, followed by culturing at 38° C. in the presence of 5% $CO_2$ gas overnight.

3. Determination of transfection efficiency (efficiency of gene transfer)

The cultured cells were rinsed three times with 1.25 ml of PBS per well, a lysed cell solution was prepared, and detection of expressed CAT was carried out using CAT-ELISA kit (manufactured by Boehringer Mannheim) according to a method for using the present kit. Since the present kit used a horseradish peroxidase-labelled secondary antibody and ABTS as a substrate, a ratio of absorbance at 405 nm/490 nm was determined. A value obtained by subtracting a blank value from a value for each group in a case of addition of pCAT-control vector, using a value for the group in a case of no addition of pCAT-control vector upon electroporation as a blank, was adopted as an amount of expressed CAT.

The results thereof are shown in FIG. 1. That is, FIG. 1 is a figure showing efficiency of gene transfer into a cell in each polypeptide-treatment group, where the ordinate shows non-treated group and each polypeptide-treatment group and the abscissa shows gene transfer efficiency expressed as a ratio of absorbance at 405 nm relative to that at 490 nm.

As shown in FIG. 1, an amount of expressed CAT in the culture dish in the C274, H296 or C·CS1-treatment group is higher as compared with that in a non-treatment group, demonstrating that efficiency of transfer of pCAT-control vector into a cell is higher.

EXAMPLE 2

1. Coating of culture dish with cell-adhesive polypeptide

A polypeptide represented by SEQ ID NO:3 (hereinafter referred to as "C274"), a polypeptide represented by SEQ ID NO:4 (hereinafter referred to as "H296") and a polypeptide represented by SEQ ID NO:5 (hereinafter referred to as "C·CS1") were each dissolved in a phosphate buffered saline (PBS) to 1 μM, respectively, which were then sterilized using a 0.22 μm filter (Millex-GV, Millipore). 1 ml/well of these solutions were added to a 24-well polystyrene culture dish (manufactured by Corning) to coat the dish at 4° C. overnight, respectively. These dishes were rinsed with 500 μl/well of a Dulbecco's modified minimum basal medium not containing bovine fetal serum prior to addition of a transformed cell described below.

2. Transfection of cell

Two culture dishes (diameter: 100 mm) of African green monkey kidney cell COS-7 which had been cultured in a Dulbecco's modified minimum basal medium containing 10% bovine fetal serum were rinsed with 10 ml of a Dulbecco's modified minimum basal medium not containing bovine fetal serum, respectively, and 3 ml of PBS containing 0.25% bovine trypsin and 0.02% EDTA was added thereto to detach cells from the culture dish. To these, 7 ml of a Dulbecco's modified minimum basal medium not containing bovine fetal serum was added, respectively, followed by centrifugation at 800 rpm for 3 minutes to collect cells. The resulting cells were suspended in 10 ml of a Dulbecco's modified minimum basal medium containing bovine fetal serum, followed by centrifugation at 800 rpm for 3 minutes to collect cells. The resulting cells were combined, suspended in 12 ml of PBS, a 5/6 aliquot of the suspension was taken and divided into two equal aliquots, which were centrifuged at 800 rpm for 3 minutes to collect cells, respectively. The resulting cells were suspended in 6 ml of PBS, followed by centrifugation at 800 rpm for 3 minutes to collect two batches of cells. One batch of the resulting cells were suspended in 1 ml of PBS containing 15 μg of pCAT-control vector (Promega) which had been aseptically prepared, and placed in an electroporation cuvette for Gene Pulser (BioRad), which was allowed to stand in ice for 10 minutes. The other batch of the resulting cells were suspended in 1 ml of PBS, and placed in an electroporation cuvette for Gene Pulser (BioRad), which was allowed to stand in ice for 10 minutes. Each batch of cells was allowed to stand in ice for 10 minutes, and voltage was applied thereto at 250 V and 960 μF. After application, the cells were allowed to stand in a cuvette in ice for 10 minutes. Thereafter, the cells were recovered into 15 ml of a Dulbeccol's modified minimum basal medium containing 10% bovine fetal serum, 1 ml/well of the cells were added to a 24-well polystyrene culture dish covered with the above polypeptide. These cells were cultured at 37° C. in the presence of 5% $CO_2$ gas overnight, the medium was removed by aspiration, and 1 ml/well of a fresh Dulbecco's modified minimum basal medium containing 10% bovine fetal serum was added, followed by culturing at 37° C. in the presence of 5% $CO_2$ gas overnight.

3. Determination of transfection efficiency (efficiency of gene transfer)

Figure 2:
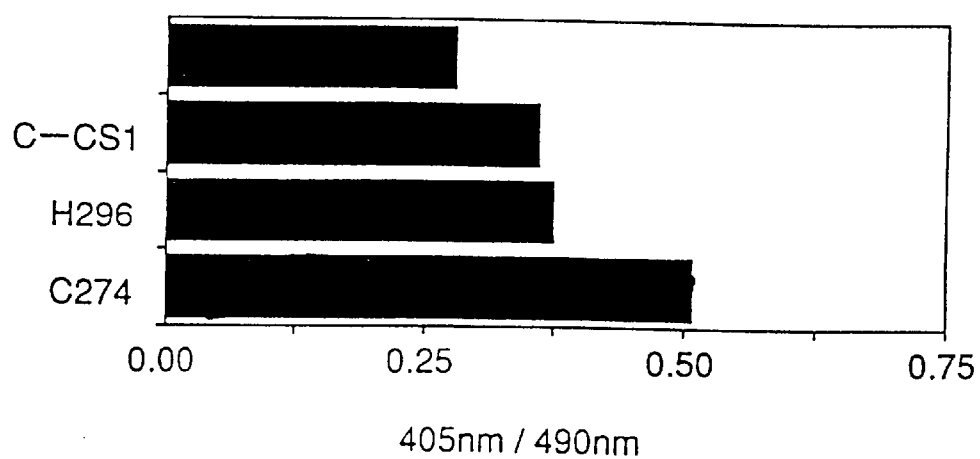
FIG. 2 is a graph showing the effect of cell-adhesive polypeptide treatment on gene transfer efficiency in the transfer of pCAT-control vector into African green monkey kidney cell COS-7-7.

The cultured cells were rinsed three times with 1.25 ml of PBS per well, a lysed cell solution was prepared, and detection of expressed CAT was carried out using CAT-ELISA kit (manufactured by Boehringer Mannheim) according to a method for using the present kit. Since the present kit used a horseradish peroxidase-labelled secondary antibody and ABTS as a substrate, a ratio of absorbance at 405 nm/490 nm was determined. A value obtained by subtracting a blank value from a value for each group in a case of addition of pCAT-control vector, using a value for the group in a case of no addition of pCAT-control vector upon electroporation as a blank, was adopted as an amount of expressed CAT. The results thereof are shown in FIG. 2. That is, FIG. 2 is a figure showing efficiency of gene transfer into a cell in each polypeptide-treatment group, where the ordinate shows non-treated group and each polypeptide-treatment group and the abscissa shows gene transfer efficiency expressed as a ratio of absorbance at 405 nm relative to that at 490 nm.

As shown in FIG. 2, an amount of expressed CAT in the culture dish in the above C274, H296 or C·CS1-treatment group is higher as compared with that in a non-treatment group, demonstrating that efficiency of transfer of pCAT-control vector into a cell is higher.

EXAMPLE 3

Preparation of kit

A kit for production of gene-transferred cells was made from C274, H296, C·CS1, PBS and a culturing dish as shown in Table 2 below. Reagents A, B and C were prepared so that the above polypeptides were adjusted with PBS to the indicated concentrations shown in the Table. Other components used are described in Example 1. In addition, all reagents A, B and C and a diluent for the reagents were aseptically prepared by pre-filtering with a 0.22 $\mu$m sterile filter.

TABLE 2

| Kit for production of transfected cell | |
|---|---|
| Reagent A . . . 100 $\mu$M C274 | 150 $\mu$l |
| Reagent B . . . 100 $\mu$M H296 | 150 $\mu$l |
| Reagent C . . . 100 $\mu$M C.CS1 | 150 $\mu$l |
| Diluent for reagents . . . PBS | 45 ml |
| 24-well polystyrene culture dish | 3 |

As described above, the present invention can overcome the problems of the previous methods for gene transfer into cells and provide a method, for production of transfected cells, having improved efficiency of gene transfer into target cells. The present invention can also provide a kit, for production of transfected cells, which is used for the method.

We claim:

1. A method for efficient production of cells transfected by cell perforation comprising the step of culturing target cells in the presence of a cell-adhesive substance after infection of a foreign gene by cell perforation into the target cells.

2. The method according to claim 1, wherein the culturing step is performed in a culture ware covered with the cell-adhesive substance.

3. The method according to claim 1, wherein the cell-adhesive substance is a cell-adhesive polypeptide.

4. The method according to claim 3, wherein the cell-adhesive polypeptide is a polypeptide having cell-adhering and/or cell-spreading activity.

5. The method according to claim 3, wherein the polypeptide having cell-adhering and/or cell-spreading activity is a polypeptide comprising an amino acid sequence represented by SEQ ID NO:1 and/or an amino acid sequence represented by SEQ ID NO:2.

6. The method according to claim 3, wherein the cell-adhesive polypeptide is selected from the group of polypeptides consisting of SEQ ID NOs:3, 4 and 5.

7. The method according to claim 1, wherein the cell-adhesive substance is poly-N-p-vinylbenzyl-D-lactoneamide.

8. The method according to claim 1, wherein the target cells are selected from the group consisting of hematopoietic stem cells, peripheral blood stem cells, umbilical blood cells, ES cells, lymphocyte and cancer cells.

9. The method according to claim 1, wherein the foreign gene is a nucleic acid selected from the group consisting of nucleic acids encoding proteins, nucleic acids encoding polypeptides, antisense DNAs, antisense RNAs, ribozymes, nucleic acids encoding intracellular antibodies and pseudogenes.

10. The method according to claim 1, wherein the foreign gene is a nucleic acid selected from the group consisting of nucleic acids encoding proteins, nucleic acids encoding polypeptides, antisense DNAs, antisense RNAs, ribozymes, nucleic acids encoding intracellular antibodies and pseudogenes and wherein the nucleic acid is incorporated into a vector.

11. The method according to claim 10, wherein the vector is a vector selected from the group consisting of retrovirus vectors, adenovirus vectors, vacciniavirus vectors and herpesvirus vectors.

12. The method according to claim 1, wherein cell perforation is performed by a method selected from the group consisting of an electroporation method, a microinjection method and a particle gun method.

* * * * *